(12) United States Patent
Van Driessche et al.

(10) Patent No.: US 8,476,476 B2
(45) Date of Patent: Jul. 2, 2013

(54) OFFGAS CLEANUP IN OLEFIN HYDROFORMYLATION

(75) Inventors: Eddy T. A. Van Driessche, Eeklo (BE); Ronald D. Garton, Baton Rouge, LA (US); Raphael F. Caers, Edegem (BE)

(73) Assignee: ExxonMobil Chemical Patents Inc., Houston, TX (US)

( * ) Notice: Subject to any disclaimer, the term of this patent is extended or adjusted under 35 U.S.C. 154(b) by 139 days.

(21) Appl. No.: 13/001,930

(22) PCT Filed: Aug. 19, 2009

(86) PCT No.: PCT/EP2009/005995
§ 371 (c)(1),
(2), (4) Date: Mar. 18, 2011

(87) PCT Pub. No.: WO2010/022880
PCT Pub. Date: Mar. 4, 2010

(65) Prior Publication Data
US 2011/0184211 A1  Jul. 28, 2011

(30) Foreign Application Priority Data

Oct. 14, 2008  (EP) .................................... 08166548

(51) Int. Cl.
*C07C 45/50* (2006.01)

(52) U.S. Cl.
USPC ......................................... 568/429; 568/451

(58) Field of Classification Search
USPC ................................ 568/429, 451
See application file for complete search history.

(56) References Cited

U.S. PATENT DOCUMENTS

| | | | |
|---|---|---|---|
| 2,667,514 A | 1/1954 | Fuqua et al. | |
| 3,455,091 A | 7/1969 | Herber et al. | |
| 4,625,067 A | 11/1986 | Hanin | |
| 5,235,112 A | 8/1993 | Nadler et al. | |
| 5,237,104 A | 8/1993 | Summerlin | |
| 5,237,105 A | 8/1993 | Summerlin | |
| 5,336,473 A | 8/1994 | Nadler et al. | |
| 5,354,908 A | 10/1994 | Nadler | |
| 5,410,090 A | 4/1995 | Beadle et al. | |
| 5,457,240 A | 10/1995 | Beadle et al. | |
| 6,437,170 B1 | 8/2002 | Thil et al. | |
| 6,960,699 B2 | 11/2005 | Totsch et al. | |
| 7,081,553 B2 | 7/2006 | Clausi et al. | |
| 2005/0215828 A1 | 9/2005 | Garton et al. | |
| 2007/0161829 A1 | 7/2007 | Van Driessche | |
| 2011/0160490 A1 | 6/2011 | Van Driessche | |

FOREIGN PATENT DOCUMENTS

| | | |
|---|---|---|
| EP | 0 183 546 | 10/1990 |
| EP | 0 643 683 | 8/1997 |
| EP | 0 835 234 | 9/2001 |
| GB | 660 737 | 11/1951 |
| GB | 702 192 | 1/1954 |
| GB | 702 222 | 1/1954 |
| WO | WO 93/24436 | 12/1993 |
| WO | WO 03/082789 | 10/2003 |
| WO | WO 2005/058787 | 6/2005 |
| WO | WO 2010/022881 | 3/2010 |

OTHER PUBLICATIONS

Scheidmeir, W. J., *Hydroformylierung von Butenen und Pentenen—Synthesen, Produkte und Möglichkeiten ihres Einsatzes*, Chemiker-Zeitung, 96$^e$ Jahrgang, (1972), pp. 383-387. (with English Abstract).
Falbe, J., "*New Synthesis with Carbon Monoxide*", Springer-Verlag, pp. 158-176 (1980).

*Primary Examiner* — Sikarl Witherspoon
(74) *Attorney, Agent, or Firm* — Leandro Arechederra, III

(57) ABSTRACT

In the hydroformylation of C5-C14 olefins with cobalt catalyst to produce C6-C15 oxygenates, where offgasses from the hydroformylation or cobalt removal step contain volatile cobalt compounds, the cobalt compounds are recovered by scrubbing the offgas with a liquid, and recycling the liquid to the cobalt removal step. Suitable scrubbing liquids are the organic cobalt-depleted hydroformylation reaction product or a downstream derivative thereof, or an aqueous solution of a $Co^{2+}$ salt, preferably such salt of formic acid.

17 Claims, 1 Drawing Sheet

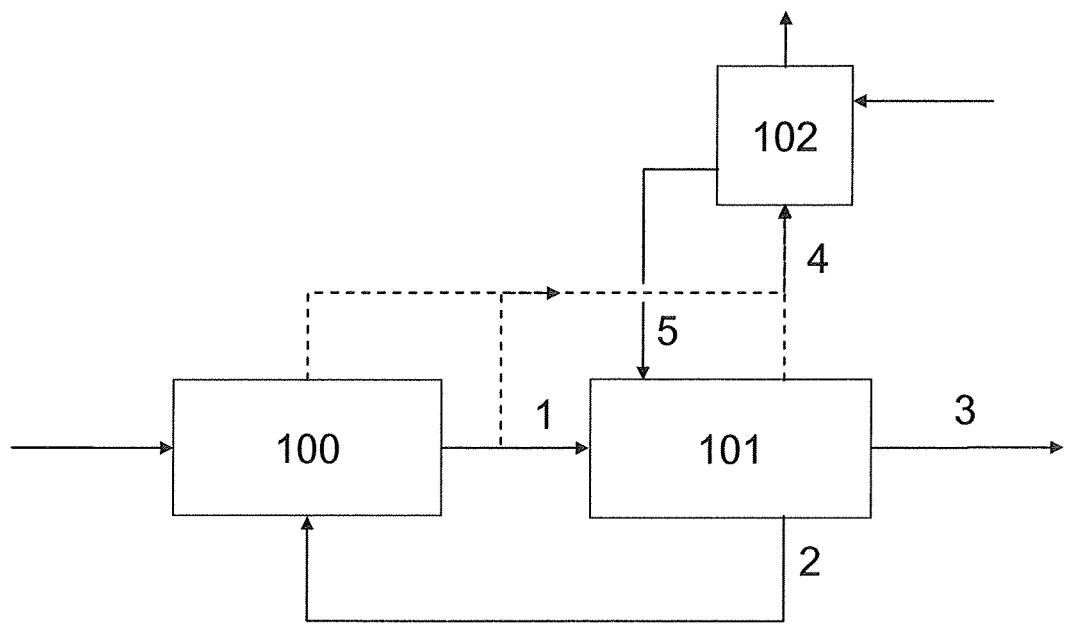

OFFGAS CLEANUP IN OLEFIN HYDROFORMYLATION

CROSS REFERENCE TO RELATED APPLICATIONS

This application is a 371 National Stage Application of International Application No. PCT/EP2009/005995, filed Aug. 19, 2009, which claims the benefit of U.S. application Ser. No. 61/092,835, filed Aug. 29, 2008 and EP 08166548.1, filed Oct. 14, 2008, the disclosures of which are herein incorporated by reference in their entireties.

FIELD OF THE INVENTION

The present invention relates to the cobalt-catalysed hydroformylation of $C_5$-$C_{14}$ olefins to produce oxygenates. This invention is useful in removing volatile cobalt from offgasses produced in and/or downstream of the hydroformylation reaction, and improving the recovery of the cobalt catalyst.

BACKGROUND OF THE INVENTION

Hydroformylation is a well-known process in which an olefin is reacted with carbon monoxide and hydrogen in the presence of a catalyst to form aldehydes and/or alcohols containing one carbon atom more than the feed olefin. It is also known as the Oxo process, or as the oxonation process. Cobalt is a preferred catalyst for the high pressure hydroformylation of $C_5$-$C_{14}$ olefinic feedstocks, in particular those that are rich in branched and internal olefins. The cobalt carbonyl catalyst typically produces oxygenated product mixtures that are richer in the usually more desired less branched isomers, as compared to the carbonyl catalysts of other suitable metals, in particular of rhodium.

The present invention is concerned with the recovery of cobalt carbonyl catalyst from the hydroformylation reaction, also known as the Oxo or oxonation reaction.

The starting liquids that are involved in high pressure hydroformylation comprise olefins which may be mixtures of olefins such as those obtained from olefin oligomerisation units. For example the olefins may be mixtures of $C_5$ to $C_{12}$ olefins obtained by the phosphoric acid or zeolite catalysed oligomerisation of mainly $C_3$ and $C_4$ olefins and mixtures thereof. $C_5$ olefins may also be present during oligomerisation, as well as traces of ethylene. Where olefin mixtures are used as feed for hydroformylation, they may have been fractionated to obtain relatively narrow boiling cut mixtures of mostly the appropriate carbon number for the production of aldehydes and alcohols with the desired carbon number. Alternatively the olefins may be obtained by other oligomerisation techniques. Such techniques include the dimerisation or trimerisation of butene using a nickel based or nickel oxide catalyst, like the Octol® process or the process described in U.S. Pat. No. 6,437,170. Others include oligomerisation processes for ethylene, propylene, pentenes and/or butenes, preferably single carbon number feedstocks and more preferably the unbranched, even more preferably terminal olefins such as butene-1, using nickel salt and involving di-alkyl aluminium halides, like the range of Dimersol® processes. Yet other oligomerisation processes may employ a zeolite or a molecular sieve oligomerisation catalyst for the oligomerisation of propylene and/or butenes and/or pentenes. The olefin products of these processes are typically branched and contain relatively low amounts of linear olefin isomers, typically less than 10% wt. The olefins may also be obtained from ethylene growth processes, such as the Shell Higher Olefins Process (SHOP) or the Ziegler process, in which case they are often straight chain, preferably terminal olefins, and are called linear alpha olefins or normal alpha olefins. The SHOP process may include a metathesis step, in which case also uneven carbon numbers may be produced. The olefins from ethylene growth may have $C_6$, $C_8$, $C_{10}$ or $C_{12}$, or even higher carbon numbers such as up to $C_{14}$, $C_{16}$, $C_{18}$ or even $C_{20}$, or they can be mixtures obtained from the Fischer-Tropsch process for the conversion of synthesis gas to hydrocarbons and which generates olefins of a range of carbon numbers, primarily containing terminal olefins but which may show some side branches along their longest alkyl chain, and which may also contain some internal olefins, linear and branched. In this case, also the higher carbon numbers may be useful starting liquids. Fischer-Tropsch olefins suitable for high pressure hydroformylation are disclosed in EP 835 234, but many other disclosures in this field may readily be found. The Fischer-Tropsch process uses syngas as the starting material, and suitable sources thereof are disclosed hereinafter.

The starting materials for the olefin oligomerisation processes mentioned above may be obtained from fluid catalytic cracking (FCC), from the steam or thermal cracking of gasses such as ethane and propane, of liquids such as liquefied petroleum gasses (LPG), of naphtha, of gasoil or heavier distillate, or even of whole crude. The oligomerisation starting material may also come from oxygenate-to-olefin processes, and from paraffin dehydrogenation processes.

The gases that are involved in the hydroformylation reaction include carbon monoxide and hydrogen, frequently supplied in a mixture that is known as synthesis gas or "syngas". Syngas can be obtained through the use of partial oxidation technology (PDX), or steam reforming (SR), or a combination thereof that is often referred to as autothermal reforming (ATR). Thanks to the water-gas-shift reaction for supplying the hydrogen, it can be generated from almost every carbon containing source material, including methane, natural gas, ethane, petroleum condensates like propane and/or butane, naphtha or other light boiling hydrocarbon liquids, gasoline or distillate-like petroleum liquids, but also including heavier oils and byproducts from various processes including hydroformylation, and even from coal and other solid materials like biomass and waste plastics, as long as these provide a carbon source and can be brought into the reaction zone. When using liquid feeds for syngas generation, a steam reformer may involve a pre-reformer to convert part of the feed to methane or other light hydrocarbon gasses before entering the actual reformer reaction. The use of coal as feedstock for generating syngas is well known, preferably via the POX or ATR route. Such syngas may be fed directly as syngas feed for hydroformylation, but also as a feed to a Fischer-Tropsch process to generate the olefin feedstocks for the hydroformylation reaction. The latter is of interest for geographic regions where the other above mentioned carbon sources, in particular oil and gas, are less abundant.

The syngas is typically present in the hydroformylation reaction in a stoichiometric excess. Upon completion of the hydroformylation (oxonation) reaction, typically a separate gas phase is present, and in addition a significant amount of gasses becomes dissolved in the liquid reaction mixture. In combination, these comprise the unreacted gaseous reactants and any gaseous inerts that may have entered with the reactants and/or the catalyst. These excess gasses are typically separated off in a high pressure separator and/or after flashing the reaction product to a lower pressure.

The high pressure offgasses may contain entrained liquid and cobalt carbonyls, because of non-ideal separations at such high pressures, and it is proposed in U.S. Pat. No. 2,667, 514 and GB 660,737 to include a scrubber on the high pressure offgas to scrub the offgas of these entrained species.

When vaporous aldehydes having three to five carbon atoms are produced, the offgasses may contain significant amounts of aldehydes. It may therefore be advantageous to employ the technique disclosed in U.S. Pat. No. 3,455,091, or in W. J. Scheidmeir, "Hydroformylierung von Butenen und Pentenen—Synthesen, Produkte und Möglichkeiten ihres Einsatzes", Chemiker-Zeitung, 96$^e$ Jahrgang (1972) Nr. 7, pp 383-387, in which the offgasses may be scrubbed with water or with a high boiling solvent, such that the C3-C5 aldehydes may be recovered.

After completion of the oxonation reaction, the metal catalyst must be removed from the reaction products because it is typically undesired in any downstream processing, such as hydrogenation.

The cobalt species that is believed to be the active form of the catalyst for hydroformylation is a carbonyl compound, typically hydr(id)ocobalt (tetra)carbonyl, $HCo(CO)_4$. Under the reaction conditions of high temperature and hydrogen partial pressure, it is believed that the following equilibrium reaction occurs, and that the equilibrium is significantly shifted to the left.

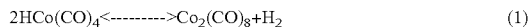

$$2HCo(CO)_4 \longleftrightarrow Co_2(CO)_8 + H_2 \quad (1)$$

The hydroformylation catalyst is typically homogeneous, hence remains in the organic product of the olefin hydroformylation reaction. $Co_2(CO)_8$ is typically soluble only in an organic medium, such as the organic hydroformylation product. $HCo(CO)_4$, however, is more versatile. It is also able to move to a water phase, if present, and dissociate as a Brönsted acid, and it has a vapour pressure, such that, at lower pressures, it may also move into a separate gas or vapour phase, if present.

Several technologies for recovery and recycle of a cobalt catalyst from the hydroformylation reaction are known.

Many of the cobalt recovery technologies comprise the conversion of the cobalt carbonyls to a water soluble salt, a step that is typically performed at a pressure that is significantly below the hydroformylation reaction pressure. Dissolved gasses separate at lower pressures from the reaction product, and volatile $HCo(CO)_4$ may therefore be present when these gasses are separated as offgasses from the hydroformylation reaction product.

When cobalt carbonyls are converted to a water soluble $Co^{2+}$ salt, carbon monoxide is liberated, typically resulting in a separate gas phase that may be separated as an offgas stream. Several of these cobalt carbonyl conversion techniques employ in addition an oxygen-containing gas as an oxidant. Air is typically used, and the air may be diluted, to address flammability concerns, with nitrogen and/or another gaseous diluent. These additional gasses further increase the amount of offgasses from the process. As the cobalt conversion in these techniques may not be complete, their offgasses may also contain minor amounts of volatile cobalt. These cobalt conversion techniques are suitably called "airless demet" when no extra oxidant is introduced, and "air demet" if an extra oxidant is used. This nomenclature is also used when air is not employed as the source of the oxidant. These cobalt conversion techniques may be preceded by a cobalt carbonyl extraction step, such as in the process disclosed in our copending patent application with attorney docket number 2008EM222. In particular the air demet technique is found to be most suitable to combine with the extraction step, because of the higher volume and energetic efficiency.

Some of the known cobalt recovery technologies make use of the volatility of $HCo(CO)_4$. It is proposed in J. Falbe, "Carbon Monoxide in Organic Synthesis" (1970), to recover volatile cobalt carbonyls from offgases, by washing the offgas either with fresh olefin or with solvents or oil. The cobalt containing olefin or solvent is then used for charging the catalyst to the hydroformylation reaction. With lower olefins, such as ethylene, propylene and butenes, GB 702,192 and GB 702,222 propose the reaction medium for offgas scrubbing under pressure, so that unreacted olefin may also be recovered and returned to the reaction.

The so-called "Cobalt Flash" process employs a low pressure stripping step to remove a major part of the cobalt catalyst from an organic cobalt-containing reaction product into a stripping gas. The volatile cobalt is subsequently absorbed from the cobalt containing stripping gas in a suitable solvent, such as the feed olefin, and recycled to the oxonation reaction. This "Cobalt Flash" process is disclosed in more detail in U.S. Pat. No. 4,625,067 (Hanin) and its many variations in U.S. Pat. Nos. 5,235,112, 5,237,104, 5,237,105, 5,336,473, 5,410,090, 5,457,240, and 7,081,553, and in European Patent 643 683 or WO 93/24436. The stripping gas, from which the volatile cobalt has been removed, is then preferably recycled by a blower or low-head compressor to the low pressure stripping step to again pick up volatile cobalt. The solvent into which the volatile cobalt was recovered by absorption, is in all the Cobalt Flash processes routed to the hydroformylation reaction, because it constitutes the major source of cobalt catalyst for the reaction. An improved cobalt absorption step is disclosed in U.S. Pat. No. 5,354,908, offering a more concentrated cobalt containing olefin stream for feeding to the hydroformylation reaction. The "Cobalt Flash" process may comprise a secondary cobalt conversion or recovery step, such as those described before, to increase the effectiveness and/or efficiency of the overall process, and wherein the remainder of the cobalt that is not stripped may then primarily be recovered, and preferably recycled, typically in a non-volatile form. The air demet technique is very suitable for this purpose, and a combination of the "Cobalt Flash" technique with the two step decobalting process as described in our co-pending patent application U.S. Ser. No. 61/092,833 was found to be highly suitable for obtaining a high level of cobalt removal and recovery from the organic hydroformylation reaction product.

In any of these cobalt removal and recovery processes as described, in particular in any so-called air demet or airless demet step that is included, or in steps wherein the pressure is let down from the high pressure hydroformylation pressure to a lower pressure, low pressure offgas streams may be generated that contain volatile cobalt carbonyls, more particularly $HCo(CO)_4$. When oxygenates are produced that have 6 or more carbon numbers, these streams typically contain only small amounts of oxygenates, so that extra steps and equipment for their recovery is typically not included.

We have found however that the volatile cobalt contained in these offgasses may create problems downstream. These offgasses may be compressed, for recycle to the hydroformylation reaction or for enabling a more commercially advantageous disposition, or they may be disposed of as such, alone or in combination with gasses from other sources, and typically as fuel gas for combustion in a furnace through a burner device. We have found that the $HCo(CO)_4$ may form solid cobalt deposits in the equipment downstream from the offgas separation, in particular in a compressor, or a control valve, or a burner device but also in the piping itself. The deposits may be in the form of dicobaltoctacarbonyl and/or as cobalt clusters and/or as cobalt metal. These deposits typically foul the equipment at undesired locations and tend to impair the proper functioning thereof, in particular of any compressor, burner, or heat exchanger that is exposed to these offgasses, and/or increase the need for maintenance interventions.

In many circumstances, a volatile cobalt absorption step, such as provided in the "Cobalt Flash" technique and which serves to capture the cobalt into a liquid that is then pumped up to high pressure and routed to the hydroformylation reaction, may not be available as part of the entire process, or the pressure of the cobalt containing offgas may be insufficient for routing it to the absorption step. Providing an additional absorption step including associated equipment to recycle the cobalt-containing absorption liquid as an extra catalyst charge to the hydroformylation reaction may bring an extra process complexity and additional investment that may not be desirable in view of the small amount of cobalt catalyst that may be recovered from the offgasses. Because of the high pressures cobalt hydroformylation processes typically operate, the cobalt-containing absorption liquid would have to be pumped up to those high pressures in order to allow its introduction into the hydroformylation reactor, which represents a significant extra investment burden.

There remains therefore a need for removing volatile cobalt from an offgas that is separated from an organic cobalt-containing hydroformylation product in a simple, effective way, by a method that is volume and energy-efficient. The current invention provides a solution to this need.

SUMMARY OF THE INVENTION

The invention provides for a process for producing a $C_6$-$C_{15}$ oxygenate by hydroformylating a $C_5$-$C_{14}$ olefin feed in the presence of a hydroformylation catalyst comprising a first metal that is cobalt, to form an organic cobalt-containing hydroformylation reaction product (1), which process comprises a demetalling step for removing cobalt from the reaction product (1) thereby producing a cobalt-containing aqueous product (2) and an organic cobalt-depleted reaction product (3), and in which process a gas stream (4) containing volatile cobalt carbonyl is separated from the reaction product (1) and the gas stream (4) is treated with an absorption liquid for absorbing at least part of the volatile cobalt carbonyl contained in the gas, thereby forming a cobalt-containing absorption liquid, characterised in that the cobalt-containing absorption liquid is recycled to the demetalling step.

By $C_5$-$C_{14}$ olefin feed is meant a feed that contains at least one olefin in the specified carbon number range. In commercial operation there are typically two or more such olefins in the feed that have a carbon number in the range. As discussed hereinafter, the feed may additionally include one or more olefins having a carbon number outside the specified range.

The invention provides a simple method for alleviating or eliminating the fouling problems, and the operational and maintenance problems that arise in consequence, which are associated with the presence of volatile cobalt in the offgasses from the hydroformylation step or from the subsequent demetalling step or steps.

The recycle of the cobalt-containing absorption liquid to the demetalling step brings the advantage that the cobalt absorbed into the absorption liquid may still be recovered as part of the hydroformylation catalyst cycle, optionally and preferably even as a cobalt carbonyl, and possibly in some processes even more preferably as $Co^{-1}$. This reduces the disposal and/or treatment needs for waste byproducts from the hydroformylation process, which may be required or desirable for an acceptable environmental performance, especially because cobalt containing waste streams typically also contain salts and/or organics, which may require further treatment steps before disposal. The invention therefore further provides a simple method for alleviating or eliminating a number of emission issues related to the hydroformylation process.

The recycle may be performed in a very simple way, such as by providing the gas treatment step at an elevated level above the receiving vessel of the demetalling step, and having the cobalt-containing absorption liquid flow to the receiving vessel by gravity. Alternatively, a liquid pump may be used in performing the recycle. Because of the respective pressures, there is no need for a high pressure pump to perform this service, and which would be required if the cobalt-containing absorption liquid was to be injected into the hydroformylation reactor. An additional advantage of recycling to the demetalling step, instead of to the hydroformylation reactor, is that the absorption liquid can be more freely chosen, because it stays downstream of the hydroformylation reaction, such that it cannot affect the reaction itself, nor occupy expensive reactor volume by diluting the reactants in the hydroformylation reaction.

The receiving vessel may be a phase separation vessel that is part of the demetalling step, such as a vapour-liquid separator, a liquid-liquid separator, or a three-phase gas/organic/water separator vessel.

BRIEF DESCRIPTION OF THE DRAWINGS

FIG. 1 shows a flow diagram of a process according to the present invention.

DETAILED DESCRIPTION OF THE INVENTION

One form of cobalt carbonyl, i.e. $HCo(CO)_4$, is known to be volatile. As a consequence, offgas streams separated from liquid hydroformylation reaction products containing cobalt carbonyls, may also contain cobalt carbonyls. Offgasses separated at high pressures, such as 200 barg or above, typically contain only small traces, if any, of cobalt carbonyl. We have found that the offgasses separated off at lower pressures may contain sufficient cobalt carbonyls to create problems downstream, primarily by depositing in undesirable locations and impairing process operations. In addition to the desire to recover such cobalt carbonyls for recycle to the hydroformylation reaction, it is equally desirable to remove the cobalt carbonyls from the offgasses before they find further use.

In a hydroformylation process including a demetalling step, offgas streams containing volatile cobalt carbonyl may be separated from the organic cobalt-containing hydroformylation product at several process locations and at several and possibly different pressure levels. Because of the limited volatility of $HCo(CO)_4$, low pressure offgasses may contain more significant amounts of cobalt than offgasses separated at higher pressures. We therefore prefer to treat, according to the present invention, offgasses separated from the organic cobalt-containing hydroformylation product (1) at a pressure of at most 50 barg, more preferably at most 30 barg, even more preferably at most 20 barg, yet more preferably at most 10 barg, at most 8 barg, at most 6 barg or at most 4 barg. The treatment of these lower pressure offgasses brings the advantage that more cobalt may be recovered and that the problems occurring downstream on the offgas streams and which are alleviated or avoided by the current invention are typically more important.

The hydroformylation process may comprise one or more recycles of offgas, improving the overall gas utilization of the process. Suitable gas recycle methods are disclosed in WO 2005/058787. A recycle of offgas typically includes a recompression of the offgas, generally up to at least the pressure of the hydroformylation reaction. The recompression equipment, such as a gas compressor and the control equipment associated therewith, may be particularly vulnerable to fouling, and the formation of cobalt deposits may be particularly harmful at various locations in the recompression equipment. It may therefore be particularly useful to treat, according to the present invention, the gasses that are separated from the cobalt-containing hydroformylation product at higher pressures, such as at 50 barg or more, more particularly 75 barg or more, even more particular 100 barg or more, yet more particularly 150 barg or more or 200 barg or more, and even more particularly 240 barg or more or 250 barg or more.

The process according to the invention may comprise the treatment for cobalt absorption of the high pressure offgasses and/or the treatment of the low pressure offgasses and/or the treatment of intermediate pressure offgasses. Pressures in the range of 3-80%, more typically 5-75% and even more typically of 7-70% of the hydroformylation reaction pressure may be considered as intermediate pressures. For a nominal Oxo pressure of 300 bar (typically expressed as gauge pressure), the intermediate pressure range may be defined as 9-240 barg, or more narrowly as 15-225 barg, or 21-210 barg. Typical intermediate pressure separators operate at 100, 120 or 150 barg.

Several offgas streams may be combined into one single treatment step. If the disposition of the different offgas streams is the same, this is preferred because only one treatment step needs to be provided, bringing simplicity and saving investment cost. If the disposition of the streams is different, such as with one or more gas recycles, it is preferred to have separate treatment steps, optionally obtaining their absorption liquids from the same source and possibly provided by the same pump because of simplicity of equipment and controls.

The invention is illustrated by the flow diagram shown in FIG. 1. In a hydroformylation reaction zone 100, olefin feed is hydroformylated in the presence of cobalt catalyst to form an organic cobalt-containing hydroformylation reaction product 1. In a demetalling step 101, cobalt is removed from the reaction product 1 to form a cobalt-depleted reaction product 3, thereby producing a cobalt-containing aqueous product 2 which is recycled to the hydroformylation reaction zone 100. As part of the overall process, at least one gas stream 4 containing volatile cobalt carbonyl is separated from the reaction product 1, and this may occur in the hydroformylation zone, in the demetalling step, or in between these two steps. In a gas treatment step 102, the gas stream 4 is treated with an absorption liquid for absorbing cobalt from the gas stream, thereby forming a cobalt-containing absorption liquid stream 5, and this stream 5 is routed to the demetalling step 101 or recycled thereto.

We have found that not all liquids are equally suitable for use as the absorption liquid in the gas treatment step according to the invention. We prefer to select as the absorption liquid a liquid characterised by having a vapour-liquid distribution coefficient for hydrocobalt tetracarbonyl at a temperature of 50° C. of at most 3.0, a dimensionless number expressed as mole fraction of $Co^{-1}$ in the vapour divided by mole fraction of $Co^{-1}$ in the liquid. Preferably we employ a first absorption liquid having a vapour-liquid distribution coefficient of at most 1.5, more preferably at most 1.0, even more preferably at most 0.6 and yet more preferably at most 0.1, at the same temperature.

The vapour-liquid distribution coefficient of a liquid for hydrocobalt tetracarbonyl may be measured, and we prefer to use the following method. A continuous hydroformylation reaction is operated in steady state with a Cobalt Flash stripper-reactor downstream thereof for stripping $HCo(CO)_4$ from the oxo product. The cobalt-containing vapour stream from the stripper-reactor contains a steady concentration of cobalt as $HCo(CO)_4$, which may readily be analysed and expressed in mole fraction or %. The vapour stream is bubbled through a scrubber vessel containing the absorption liquid and kept at the prescribed measuring temperature. The vapour stream from the scrubber vessel is led to an absorber tower or vessel for absorption of any cobalt remaining therein. The cobalt in this vapour from the scrubber vessel is also present as $HCo(CO)_4$ and its concentration may also be analysed. Equilibrium is reached when the two vapour streams contain the same cobalt concentration and the absorption liquid in the scrubber vessel is saturated with $HCo(CO)_4$. The liquid is then sampled and analysed for its cobalt content, and converted also into mole fraction or %. The ratio of the cobalt concentration in the vapour divided by the cobalt concentration in the liquid gives the "apparent" vapour-liquid distribution coefficient for hydrocobalt tetracarbonyl for this particular absorption liquid and at the temperature of measurement. A lower "apparent" distribution coefficient is obtained at a lower temperature.

It is therefore preferred to operate the absorption step at a temperature in the range of 10-100° C., preferably 20-90° C., more preferably 25-80° C., yet more preferably 30-70° C. and even more preferably 35-60° C.

We have found that the absorption liquid may be organic. We prefer to use as organic absorption liquid an organic liquid that is already present in, or related to the hydroformylation process according to the invention, thereby avoiding concerns of the process being contaminated with unfamiliar streams or species.

In one embodiment, we prefer that the absorption liquid is a part of the organic cobalt-depleted reaction product (3). This stream is most readily available and recycling part of this reaction product (3) over the absorption step and into the demetalling step creates a fairly short recycle loop with the least effect on the additional hydraulic loads of the equipment items, in particular of any downstream steps as described further herein.

In another embodiment, we prefer to use as the absorption liquid an organic liquid that is generated further downstream from the demetalling step.

The invention therefore further provides a process wherein the organic cobalt-depleted reaction product (3) is separated into at least a light hydroformylation fraction and a heavy hydroformylation fraction, and the absorption liquid is at least a part of (i) the light hydroformylation fraction or of (ii) the heavy hydroformylation fraction. These light and heavy hydroformylation fractions bring the advantage that they are less prone still to contain any remaining oxidant, if an oxidant is used in the demetalling step. We prefer to use a part of (ii) the heavy hydroformylation fraction, because this is less volatile than the light hydroformylation fraction (i), and thus less of the organic absorption liquid is vaporised and carried with the offgas from the absorption step. The use of this heavy fraction also minimises the energy requirement associated with this organic recycle in the overall oxygenate production process.

The organic cobalt-depleted reaction product (3) produced in the demetalling step, or at least part of it, is typically subjected to a hydrogenation step, wherein typically aldehydes and/or formate esters are converted into alcohols. This hydrogenation may be performed on the organic cobalt-depleted reaction product (3) itself, or a part thereof, but it may also be performed on a stream obtained by first separating a light and/or heavy hydroformylation fraction therefrom. The hydrogenation step may be preceded by an additional washing step, to remove last traces of catalyst metal, by a hydrolysis step, to convert formate esters and/or acetals by hydrolysis into alcohols and/or aldehydes, and/or by one or more distillation steps to e.g. separate aldehydes from the stream prior to hydrogenation, for instance for conversion of such aldehydes into carboxylic acids.

The invention therefore further provides a process wherein the absorption liquid is a part of a hydrogenation product obtained by hydrogenating at least part of the reaction product (3) formed in the demetalling step.

The hydrogenation step may be followed by distillation of the hydrogenation product into different fractions. We have found that these fractions are also suitable as absorption liquid in the absorption step. The invention therefore further provides a process further comprising hydrogenating at least part of the reaction product (3) to form a hydrogenation product, separating at least part of the hydrogenation product into a light hydrogenation fraction and a heavy hydrogenation fraction and wherein the absorption liquid in the gas treatment step is at least a part of (iv) the light hydrogenation fraction or of (v) the heavy hydrogenation fraction.

Also mixtures of the suitable organic absorption liquids described herein may be used.

We have found that the absorption liquid may alternatively be aqueous. Water may be used, optionally also containing a first acid, such as acetic acid, but more preferably formic acid, because formic acid may already be present as a byproduct from the hydroformylation reaction. When an acidic absorption liquid is used, we prefer to route the gasses from the treatment with the absorption liquid to a second treatment with an alkaline water stream, to reduce acid corrosion in the equipment downstream.

We have found that the absorption of cobalt carbonyls with water or an aqueous stream may be improved by further providing a metal cation. The invention therefore further provides a process wherein the absorption step uses as the absorption liquid an aqueous solution of a metal salt of a second metal and a second acid having a pKa of at least 1.5 at 25° C. The pKa of the second acid, defined as in formula (2), and if a dibasic or polybasic acid is used it should be the first pKa of the acid, is preferably higher than the pKa of hydrocobalt carbonyl, which is believed to be 1.14 at 25° C.

$$pK_a = -\log_{10}[H^+][anion^-] \quad (2)$$

In principle, the salt of any acid fulfilling this requirement is suitable for improving the absorption of the cobalt carbonyl. However, the recycle of the cobalt-containing absorption liquid to the demetalling step may thus introduce the first acid and/or the anion of the second acid into the cobalt catalyst cycle. In several cobalt catalyst cycles, the acid and/or the anion may then be introduced into the hydroformylation reaction. We therefore prefer to use acids of which the anion does not behave as too strong a base. We therefore prefer to use an acid having a first pKa of at most 7, preferably at most 6, more preferably at most 5, and most preferably at most 4. This offers the important advantage that such acids and/or their anions have little to no effect in the hydroformylation reaction, where under conditions of hydrogen partial pressure and temperature the hydro cobalt carbonyl, i.e. the acidic form of the cobalt carbonyl, is restored. In the presence of the free water phase, acids with strong basic anions could cause at least partial neutralisation of the cobalt carbonyl during the hydroformylation, into a form that is inactive for the hydroformylation reaction.

We prefer to use an organic acid as the first and/or second acid, because these do not introduce heteroatoms into the process. Suitable acids are propionic acid ($pK_a$=4.87), acetic acid ($pK_a$=4.75) and formic acid ($pK_a$=3.75). Most preferred is formic acid, because formic acid, or a derivative thereof, is an expected component in the hydroformylation product, either as such or in the form of the formate ester of the product alcohol. The use of formic acid as first acid and/or second acid, preferably as both acids, therefore does not add a separate burden in the further treatment steps of the hydroformylation product, for the removal of the acid or of its ester.

In principle, any metal cation is suitable as the second metal of the metal salt for improving the absorption of the cobalt carbonyl. However, the recycle of the cobalt-containing absorption liquid to the demetalling step introduces the metal cation into the cobalt catalyst cycle. It is preferred to operate a cobalt catalyst cycle that operates as much as possible as a closed loop, thereby reducing or eliminating the need to dispose of sidestreams, especially those containing organics and/or cobalt. We therefore prefer to use cobalt also as the second metal in the absorption liquid, typically in the form of $Co^{2+}$. The most preferred metal salt in the aqueous absorption liquid is therefore cobalt formate.

We prefer to use as absorption liquid at least a part of a cobalt-containing aqueous product coming from the demetalling step. By preference the cobalt in this aqueous product is primarily present as a $Co^{2+}$ salt, and any cobalt carbonyl is preferably only present in a low concentration or more preferably absent. This reduces the risk of impairment of the absorption of the cobalt carbonyls from the gas phase into the aqueous absorption liquid.

A suitable cobalt-containing aqueous stream for using a part of as absorption liquid is provided in the "air demet" or "airless demet" decobalting methods that were described hereinbefore, wherein the cobalt carbonyl hydroformylation catalysts are converted to a water soluble $Co^{2+}$ salt and are separated from the organic cobalt-depleted hydroformylation reaction product (3). Any one of these two decobalting methods may optionally be used in combination with an upstream cobalt carbonyl extraction technique as explained for air demet in our copending application U.S. Ser. No. 61/092,833, and/or in combination with a cobalt carbonyl stripping step, such as the "Cobalt Flash" process described elsewhere in this document, in one of the many different embodiments thereof that are described in the references cited in that section.

The invention therefore provides for an embodiment wherein the demetalling step comprises
(a) contacting the reaction product (1) with an aqueous solution of a third acid to form an aqueous solution of the cobalt salt of the third acid as the cobalt containing aqueous product (2) and the organic cobalt-depleted reaction product (3).

One option is to employ an "airless demet" step as described. As a preference, the invention further provides for a process wherein the contacting (a) of the hydroformylation reaction product (1) is performed in the presence of an oxygen-containing gas or an oxygen-donating compound, i.e. an "air demet" step. A suitable air demetalling step is disclosed in our copending patent application PCT/EP2008/053783, which published as WO 2008/128852.

The third acid preferably corresponds to the same criteria as applied to the first and the second acid. It is a preference of these embodiments that the third acid is the same as the first acid and preferably also the same as the second acid.

We have found the combination of the process according to the current invention with the two-step demetalling technique and the cobalt recycle method described in our copending application U.S. Ser. No. 61/092,833 as particularly useful. The phase separation and demetalling steps of that combined process generate several offgas streams from at least one of which the removal of part of the contained cobalt carbonyls is advantageous.

The invention therefore provides for a process wherein the demetalling step comprises (b) contacting the organic cobalt-containing hydroformylation reaction product (1) with an aqueous solution of a salt of a third metal with a fourth acid having a pKa of at least 1.5 at 25 C, such that part of the cobalt is extracted as cobalt carbonyls into an aqueous solution, to form an aqueous solution (5) comprising the metal salt of cobalt carbonyl, and wherein the contacting (b) is performed prior to contacting (a) when contacting (a) is present. This extraction step (b) is preferably operated at a temperature in the range of 50-150° C., more preferably from 80 to 120° C., and typically about 100° C. The pressure is preferably sufficient to prevent the water from boiling at the operating temperature, but may be selected higher in order to provide sufficient driving force for liquid flows, in particular for the organic reaction product, such that pumps are not needed. The pressure is preferably in the range of 2-15 barg, more preferably of 5-12 barg or 6-11 barg and typically around 8 barg.

Many acids are suitable as the fourth acid, but we prefer to use organic acids. Suitable organic acids are propionic acid, acetic acid and formic acid. We prefer to use an acid that is less soluble in the organic phase, because less acid is removed from the demetalling step with the cobalt-depleted organic reaction product (3). We therefore prefer to use acetic acid or formic acid, but most preferably formic acid because of its lower solubility in the organic reaction product. Formic acid is a byproduct from the hydroformylation reaction, because formate esters are also formed in hydroformylation, and upon hydrolysis, these formate esters may generate formic acid. The process steps and equipment downstream of hydroformylation are therefore adapted to handle the presence of formic acid and formate esters in the hydroformylation reaction product. Other acids and/or their esters would create extra process burdens and extra product quality concerns. We therefore prefer to use formic acid as the fourth acid in the demetalling step.

The fourth acid preferably corresponds to the same criteria as applied for selecting the third and/or the second acid, and more preferably also for selecting the first acid. It is a preference of these embodiments that the fourth acid is the same as the third acid, more preferably that the fourth acid is also the same as the second acid, and even more preferably also the same as the first acid. This brings the advantage that the process has only to cope with not more than two acids, and preferably not more than one acid.

The third metal is preferably also cobalt, such that the process does not have to cope with an extra metal.

The aqueous solution (5) of the metal salt of cobalt carbonyl is preferably recycled to the hydroformylation reaction, thereby providing a simple, effective and volume-efficient cobalt catalyst cycle. If the third metal is also cobalt, more cobalt is provided to the hydroformylation reaction for the same amount of metal salt solution that is recycled.

The extraction step may be operated as a single step in co-current mode with respect to the two liquid phases. However, counter-current operation may also be provided and is preferred because it overcomes the equilibrium constraint of a single co-current step. We prefer to operate with a weight ratio of aqueous solution to organic hydroformylation product of from 3 to 30%, preferably from 5 to 20%, more preferably from 6 to 16%, even more preferably from 7 to 14%, yet more preferably from 8 to 12% and most preferably from 8 to 11%, i.e. about 9 or 10%.

The aqueous solution feed to the extraction step (b) preferably contains at least sufficient metal cations to extract all the cobalt carbonyl anions available in the hydroformylation reaction product before extraction. Assuming all cobalt is present as $HCo(CO)_4$, the stoichiometric amount of cations is equivalent to half the amount of cobalt present in the reaction product entering the demetalling step. We prefer to operate without any excess, ideally, but because of control difficulties we may allow a stoichiometric excess in the range of 5-50%, preferably 6-30%, more preferably 7-20%, even more preferably 8-15%, yet more preferably 9-12%, most preferably about 10%.

In "air demetalling", we prefer to use temperature conditions of 60-130° C., preferably 65-100° C., more preferably 70-82° C. We prefer to operate at a pressure in the range of 1-15 barg, preferably 2-10 barg, more preferably around 7 barg at the point where the oxygen-containing gas is introduced, and around 2.5 to 3 barg at the point where the offgas is separated from the two liquid phases, or at a pressure sufficient to allow the offgas to be introduced, optionally after treatment with an absorption liquid according to the invention, into the site fuel gas system or into a furnace fuel gas line. A higher pressure helps to introduce oxygen from the gas into the liquid phases, in particular into the water phase. For the same reason, interfacial area between the different phases is preferably increased, if necessary by one or more static mixers or by having a packing provided in the equipment, or by agitation. We prefer to operate with a stoichiometric excess of the third acid relative to the amount of cobalt that is present in the organic feed to the "air demet" step, and more preferably with an excess in the range of 50-150%, even more preferably 60-120%. A typical residence time for the organic liquid in "air demet" is in the range of 2-10 minutes, preferably 3-5 minutes, more preferably about 4 minutes. The oxygen or oxygen-donating compound is preferably present in stoichiometric excess compared with the amount of cobalt present, albeit more preferably avoiding too high an excess in order to limit side-reactions such as oxidation of aldehyde. We prefer to operate with a stoichiometric excess in the range of 20-100%, more preferably 30-80% and even more preferably 30-70% or 30-50%. When the cobalt concentrations are low, such as below 1500 ppm by weight based on the total organic stream obtained from the hydroformylation reaction, it may be more convenient to operate at higher stoichiometric excess rates in order to maintain good control capabilities. When using an oxygen-containing gas, we also prefer to use a flammable diluent, such as natural gas or methane, to keep the air/diluent mixture above its upper flammable limit. More details of this technique are disclosed in our copending application PCT/EP2008/053783, which published as WO 2008/128852. We prefer this diluent to be low in sulphur, such as less than 1 ppm by weight, so that oxidation of sulphur to water soluble sulphoxide and further to sulphate, and build-up thereof in the water loop of the process is minimised. Also chlorine or chloride is desirably limited to a similar value.

We prefer to perform the separation of the two liquid phases in the demetalling step according to the invention with the help of a coalescer, so that the amount of water entrained with the organic phase, and which may still contain some cobalt, is minimised. A coalescer is a device that is employed to facilitate the separation of two liquid phases. A problem with separating two liquid phases can be that the density difference, which drives the separation, is often rather small. In this situation the smaller droplets travel slowly through the continuous phase (according to Stokes' Law) and in an empty vessel, they have to travel all the way to the bottom (or the top) before they start agglomerating (i.e. coalescing) to form larger droplets and ultimately separate out as a separate continuous phase. In a coalescer, horizontal (or substantially horizontal) baffles may be provided within the vessel in order to reduce the distance the droplets must travel before they can agglomerate, and thus make the separation more effective and volume-efficient. A preferred coalescer design comprises a drum with a number of parallel baffles inside, which are horizontal or slightly inclined from the horizontal. Small droplets will only need to travel to the baffle that is just below or above them, where they will form larger droplets (by coalescing with each other) which then will travel to the end of the baffle and from there will move with the faster speed of the larger droplet to the bottom or top of the vessel where the continuous separate phase is formed and removed through the outlet nozzle. The benefit of using a coalescer in the present invention is that the entrained water content of the cobalt depleted organic reaction product (3) will be reduced, if not eliminated. Any free water remaining in the cobalt depleted organic reaction product (3) may contain cobalt, which is then lost from the catalyst cycle and may cause problems downstream, e.g. in the subsequent hydrogenation step. Another embodiment of a coalescer may be one where the fluid containing small droplets of a different phase is pushed through a high porosity solid such as a packing or crinkle-wire-mesh-screen that is made of a material to which the droplet phase has a high affinity or wettability. The small droplets then tend to adhere to this easily wettable material and coagulate to form bigger droplets, which are then released from the material and readily separate into a continuous phase that can be drawn off. We have found also that a hydrophobic material may be very effective in coalescing fine water droplets in an organic stream. We have found that a Pall PhaseSep Coalescer, using pleated fluorocarbon as the coalescer medium and obtainable from Pall Corporation, is a very effective method for removing a haze of about 0.3 wt % water from a hydroformylation reaction product and producing a clear organic product after separation of the coalesced free water phase, and is able to achieve this separation with a very small residence time of the reaction product in the coalescer medium, for example of only 0.5-0.6 seconds. This embodiment using a high porosity solid may take the form of a filter, and may be included in the above described coalescer as a prefilter. Its performance and life time is improved by providing a pre-filter upstream for removal of fine solid particles, which would impair the function of the coalescer over time. Particulate matter removal using an absolute pre-filter of 15 to 20 μm, or even a 2 μm pre-filter may be advantageous. We have found that it is advantageous to use a coalescer to avoid an additional washing step, because such a washing step introduces diluent water into the catalyst cycle which then needs to be removed there from, typically incurring the consumption of more energy, and if the separated water cannot be recycled as wash water to the washing step, additionally creating a disposal problem.

It is understood that the demetalling reactions are competing with the formation of cobalt clusters, presumably according to reaction (3) as the first steps, but which include further derivative cobalt carbonyl compounds having more cobalt atoms and fewer CO fractions, down to a level where essentially only cobalt metal is present.

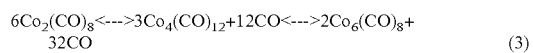

(3)

The solubility of these cobalt carbonyl compounds in the organic phase reduces as they contain fewer and fewer CO moieties in the molecule, to the point that the species come out of solution and form solid particles. While the $Co_4(CO)_{12}$ is still considered as oil-soluble, the next form $Co_6(CO)_8$ is considered as being insoluble. These particles may deposit or adhere to parts of the equipment, and often build up as a shiny metal layer recognised as "cobalt plating".

We have found that the cobalt clustering and/or plating reactions are characterised by high activation energy, such as at least 40 kcal/mole. We therefore prefer to use demetalling steps that are operated at lower temperatures, such as "air demetalling", rather than "airless demetalling" which needs higher temperatures of typically 140-190° C., more particularly 150-164° C.

We also have found that it is preferable to operate the demetalling step, especially any higher temperature airless demetalling but also including a lower temperature air demetalling step, under a minimum partial pressure of 0.2 MPa of CO, such that the cobalt carbonyl decomposition reactions and the plating reactions (3) are pushed sufficiently to the left, or even inhibited, and more cobalt ends up as $Co^{2+}$. These acid demetalling steps are preferably operated with an interfacial area between water and organics of at least 60 $cm^{-1}$, more preferably at least 100 $cm^{-1}$ or 150 $cm^{-1}$, even more preferably at least 200 $cm^{-1}$, as obtainable by one or more static mixers, and yet more preferably as high as 380 $cm^{-1}$ or more, for example up to 2000 $cm^{-1}$ when using an agitated system. This interfacial area is preferably created from the moment the feeds are subjected to conditions where the carbonyls are unstable (such as high temperature, low CO partial pressure, introduction of the acid solution and optionally the oxygen or oxygen-donating compound) in order to increase the selectivity to $Co^{2+}$. While cobalt cluster formation may be minimised, it may not be totally avoided. By providing strongly turbulent flow in the demetalling step, the particles that are fanned are carried with the turbulent flow downstream to a separator or settler, where the gas, water and organic phases are allowed to settle and separate, and where solid deposits are less of a nuisance and may be allowed to build up before equipment performance is impaired. Such cobalt deposits, including "cobalt plating", in the demetalling section can be removed chemically as explained in WO2005/058787 as a method for cleaning the hydroformylation reactors, provided the demetalling equipment is made of suitable construction materials that are able to withstand the aggressive nature of the chemicals used in this cleaning process. For details on suitable construction materials, we refer to WO2005/068787. The cleaning requires the equipment to be taken out of service, and therefore it is preferred to have the solids depositing at locations in the process equipment where the process performance is less readily impaired by them. This reduces the cleaning frequency and therefore increases equipment availability.

In order to increase turbulence, we prefer to have additional gaseous components present in the demetalling step. We have found that the addition of gas may readily increase the oil-water interfacial area by a factor of at least 2 or 3. The addition of air in the "air demetalling step" is therefore highly advantageous, especially when a diluent is used as described below. If insufficient gas is available from the flashing of the liquids because of the pressure letdowns from upstream, additional gas may be added. Any gas streams are suitable for this purpose, but portions of one or more of the offgas streams that may be separated at higher pressure levels from the hydroformylation reaction product before the demetalling step are particularly suitable. We prefer to use slipstreams from the offgasses coming from an intermediate pressure separator and/or from a high pressure separator that may be operated between hydroformylation and demetalling. We have found that such CO-containing gasses work better when the partial pressure of CO in the demetalling step is kept below 3 bar absolute, preferably below 2 bar absolute and more preferably below 1 bar absolute. Static mixers may also be used to increase turbulence, either alone or in combination with the addition of gas. When a part or the entirety of an offgas, which was separated at a higher pressure from the reaction product, is reintroduced into the liquid reaction product at a lower pressure to increase turbulence, the offgas may be treated for cobalt absorption according to the invention before the reintroduction and/or the offgas may be treated in a single treatment step together with the offgas separating from the reaction product at the lower pressure.

We have found that the aqueous $Co^{2+}$ solutions obtained from these acid demetalling steps are very suitable absorption liquids for treating the gasses according to the current invention. We have found that by using part of these solutions as absorption liquids in an offgas treatment step and recycling the resulting cobalt-containing absorption liquid to the acid demetalling step reduces the acid requirement in this demetalling step.

The "air demetalling" introduces air into a closed system full of flammable materials. It may therefore raise a safety concern. This is readily controllable in steady state operation, but needs special precautions for unsteady operations, such as with process upsets, grade switches, and the like. These problems are addressed in our copending patent application PCT/EP2008/053783, which published as WO 2008/128852.

Make-up hydroformylation catalyst may need to be introduced into the process, e.g. when the catalyst concentration needs to be increased, or when a part of the catalyst has been lost from the process or deposited inside the equipment and needs to be replaced. We have found that in the process according to the invention such a make-up of catalyst metal is most conveniently provided as a water soluble salt of the cobalt with a fifth acid, and this is preferably added into one of the aqueous recycles that are preferably foreseen as part of the demetalling step, including the treatment for absorption of volatile cobalt carbonyl that is part of the current invention. If any of the recycle streams in the demetalling step or to the hydroformylation reaction do not recycle all the amount of the stream that is available, and thus part of any of those streams is discarded, there is a continuous withdrawal of cobalt catalyst from the process. This will cause a decrease of the catalyst concentration in the hydroformylation reaction, unless a regular discontinuous or a continuous make-up is provided. Such make-up is preferably added as described hereinbefore. However, it is understood that other conventional alternatives for cobalt catalyst make-up are also suitable. Examples are the introduction of organic soluble cobalt salts, such as cobalt oleate, stearate, palmitate, naphthenate, or cobalt tallate, or cobalt hofate, wherein the hofate is the term used when using the heavy acids formed in the oxo process by e.g. the Cannizarro reaction or by the direct carbonylation of the olefin with water and CO, or by aldehyde oxidation. Other more complex make-up options involve other cobalt compounds, such as $CoCO_3$, or more typically $Co_2O_3$. These compounds may be preformed to cobalt carbonyls in a separate preforming reactor before the resulting carbonyls are fed to the hydroformylation reaction.

It may occur that an undesired metal finds its way into the process, such as by corrosion of the equipment or by introduction as a trace element in any of the feed streams. Such a metal may then convert to a water soluble form in any of the demetalling steps, and possibly impair the reactions that the catalyst metal is supposed to participate in. In such circumstances, a portion of any of the water streams containing this undesired metal, but also the catalyst metal, may need to be removed from the system, either occasionally or as a continuous slipstream. This may create another need for more make-up of the catalyst metal, preferably as hereinbefore described.

As the fifth acid, many acids are suitable, but we prefer to use an acid having a pKa of at least 1.5 at 25° C. The same pKa criteria as for the selection of the first acid apply to this fourth acid. We prefer to use an organic acid as the fifth acid, such as propionic acid, acetic acid or formic acid. We prefer this fifth acid to be the same as the first acid, such that there is no interference between different acids in the various process steps. Most preferred is that the first, the second, the third, the fourth and the fifth acid are all the same. These acids then are preferably all propionic acid, acetic acid, or formic acid. Acetic acid and formic acid are more preferred, and formic acid is most preferred because it is indigenous to high pressure cobalt hydroformylation processes. However, when the first acid, the second, the third and/or the fourth acid is formic acid, We prefer to use acetic acid as the fifth acid because the cobalt salt thereof is more readily available and because cobalt acetate is more soluble in water than cobalt formate, and the amount of water introduced with the cobalt make-up can thereby be minimised. We have found that typically the amounts of acetic acid introduced as cobalt acetate are reasonably low, and when introduced into a process using formic acid in its demetalling steps, because of the higher affinity of acetic acid to the organic phase as compared to formic acid, such amounts are conveniently and sufficiently quickly removed from the process with the cobalt-depleted organic reaction product (3). Another advantage of using acetic acid as the fifth acid is that the aqueous $Co^{2+}$ solutions in the catalyst system may be more concentrated before risking precipitation of cobalt formate, thanks to the higher solubility of cobalt acetate. It is therefore the preferred source of cobalt for the initial startup of a hydroformylation process that can accommodate an aqueous catalyst make-up. Yet another advantage for using cobalt acetate for catalyst make-up is that cobalt acetate preforms faster to the carbonyl form than cobalt formate. It is therefore preferential to feed to a preformer reactor or to the hydroformylation reactor a water stream that contains at least part of the cobalt as cobalt acetate, instead of only as cobalt formate. The use of cobalt acetate may reduce the risk of precipitation of cobalt formate, particularly when the amount of water phase introduced is small, and the amount of free water reduces because of the increasing water solubility of the organic phase, such as in a series of hydroformylation reactors where the nature of the organic phase changes as the reaction proceeds.

When an aqueous solution of cobalt is recycled to the hydroformylation reaction, we prefer that the amount of aqueous solution is at least 3% and at most 30% by weight based on the weight of the olefin feed to the hydroformylation reaction. It is preferred to avoid excessive amounts of water passing through the hydroformylation reaction, because it reduces the volume available for the organic phase in which the reaction occurs, and thus reduces the volumetric efficiency of the hydroformylation reactor, but also pulls more cobalt away from the organic phase where the reaction occurs. Provided the hydroformylation reactors are suited to accommodate it, we prefer to assure there remains a free water phase present at all times in the hydroformylation reaction and throughout the entire hydroformylation reactor, but we prefer to minimise the amount of free water present for the reasons explained. It should be understood that water is typically scarcely soluble in many feedstocks that may be hydroformylated, such as higher olefins in the $C_6$-$C_{14}$ range, but that typically the water solubility of the corresponding hydroformylation products is significantly higher. The organic phase in the hydroformylation reaction therefore develops a higher affinity for water as the reaction proceeds, and more water may become dissolved. We prefer to add sufficient water, such that there remains a free water phase present in the hydroformylation reaction product. This brings the advantage that any species present in the hydroformylation reaction that is strictly water soluble and would precipitate without a free water phase present, may remain in solution throughout the oxo reaction. We prefer therefore to use an amount of water that is also above the solubility of water in the organic product of the hydroformylation reaction. This depends on the carbon number of the alcohol produced, with lower carbon number alcohols needing more water because of the higher solubility of water in their oxo product. We prefer that the amount of aqueous solution recycled to the hydroformylation reaction is at least 3% and at most 25% by weight based on the weight of the olefin feed to the hydroformylation reaction, more preferably, on a weight basis, from 4% to 20%, even more preferably from 5 to 15%, most preferably from 6 to 13%, such as from 7 to 12%, and typically about 10%, more preferably about 8%.

We prefer to cool the hydroformylation reaction product, which is typically at a temperature of from 150-200° C., down to a temperature of from 30-60° C., and we prefer to perform this cooling while the product remains at high pressure. We have found that when there is free water present in the hydroformylation reaction product, cobalt carbonyls dissolved in this water phase are driven by this cooling step into the organic phase, and the cobalt concentration in the water phase may drop significantly. This effect is more pronounced at a higher pressure.

When a free water phase is present in the hydroformylation reaction product and in particular when the demetalling step comprises an extraction step (b) for cobalt carbonyls by contacting the organic cobalt-containing hydroformylation reaction product with an aqueous solution of a salt of a third metal with a fourth acid having a pKa of at least 1.5 at 25 C, we prefer to remove most of this free water phase in a separation step before the hydroformylation reaction product (1) enters the cobalt carbonyl extraction step (b). The invention therefore provides a process wherein, prior to the demetalling step, an additional separation step is provided comprising separating free water from the hydroformylation reaction product to form the organic cobalt-containing hydroformylation reaction product (1) as feed for the demetalling step.

In the additional, separation step, a separate gas phase is typically also separated off, and this offgas stream may contain volatile cobalt. This offgas stream may therefore be the gas stream (4) that is treated for cobalt carbonyl absorption according to the invention, either alone or in combination with other gas streams from other parts of the hydroformylation and/or demetalling steps.

In a further embodiment, and in particular when the cobalt carbonyl extraction step (b) is present, we prefer to operate this additional separation step under a partial pressure of carbon monoxide of at least 1.5 bar, preferably at least 2.5 bar, and more preferably at least 3 bar. Typically this step operates at a pressure of 10-100 barg, and preferably at least 15-20 barg, to avoid the need to provide additional liquid pumps downstream. Because of the amount of CO coming with the reaction product, the partial pressure of CO in the additional separation step is typically at least 7 bar, preferably at least 10 bar. This brings the advantage that the disappearance of cobalt carbonyls, by conversion into $Co^{2+}$ or cobalt clusters, is minimised during the separation step, such that more of the cobalt carbonyl may be available for extraction and recycle downstream.

The cobalt-containing absorption liquid formed in the process according to the present invention may be recycled to any suitable location in the demetalling step, such that the cobalt recycled may continue to participate in the catalyst cycle over the hydroformylation or oxo reaction. When a cobalt carbonyl extraction step (b) is present, we prefer to add the cobalt-containing absorption liquid to the carbonyl extraction step because, if the cobalt absorbed into the liquid remains present in a carbonyl form, at least part of this cobalt carbonyl may be recovered as the carbonyl form, and added to the cobalt carbonyls that may be recycled to the hydroformylation reaction. However, if the amount of cobalt in the absorption liquid is low, we prefer to route the cobalt-containing absorption liquid from the absorption step to the downstream and second demetalling step (a) that is preferably present with a carbonyl extraction step (b). This avoids introducing an extra volumetric load, depending on the selection of the absorption liquid, being either an aqueous or an organic phase into the extraction step, into any of the steps in the demetalling step, and which may be negatively affected by the different oil/water ratio.

The process according to the invention is suitable for combination with the "Cobalt Flash" catalyst cycle mentioned above, in all its variations and in both of the alternative operating modes that are described in U.S. Pat. No. 5,237,105 (Summerlin). The treatment step for absorbing volatile cobalt carbonyl may be applied to the offgasses generated in the "air-demet" steps provided either upstream or downstream of the stripping step. It may also be applied in the combinations described in U.S. Pat. No. 5,410,090 (Beadle et al) wherein an airless cobalt demetalling step is provided upstream or downstream of the Cobalt Flash stripping step.

The Cobalt Flash alternative operating mode having a demetalling step already upstream of the stripping step is typically called the "demet" mode, and the alternative where the stripping step is located as the upstream step is typically called the "Cobalt Flash" mode. Lighter grades are preferably processed in demet mode, and heavier grades preferably in Cobalt Flash mode. We have found that in demet mode, more particularly with air demet, any sulphur present, such as coming in with the feed olefins, may partly oxidise in the demet step to water soluble species such as sulphoxide and/or sulphate, which preferentially may move into the water phase. In particular thiophene, which may be present in a hexene feed from propylene oligomerisation, for example at a level of 18 ppm by weight of sulphur, readily converts in this manner. The sulphate helps to keep $Co^{2+}$ in solution, above the solubility limit of cobalt formate. In the preformer reactor, the sulphoxide or sulphate may partially reconvert to organic sulphur which moves then to the organic phase. We have found that any palladium catalyst used in the preformer reactor appears not to be affected by such forms of sulphur. We have also found that in air demet, when insufficient oxygen is present, a fine black powder may form, typically as $CoS_2$, which may cause fouling and particularly filter plugging downstream. Any sulphoxide or sulphate entering the downstream hydrogenation step may also convert to an organic sulphur compound.

The Cobalt Flash technique is known for having a closed water loop. In the Cobalt Flash "demet" mode, also the organic stream over the preformer is mainly operating in a closed loop. The presence of the organic stream offers the advantage that any $Co_2(CO)_8$ formed becomes dissolved in the organic medium, whereby precipitation of crystals of $Co_2(CO)_8$ on the catalyst is avoided. Any suitable organic liquid may be used in the preformer organic loop, but preferably a liquid containing a $C_5$-$C_{13}$ alcohol. We prefer to use an organic liquid that is able to dissolve a minimum amount of water at the coldest point in the cycle, such as at least 2% wt, preferably at least 3% wt, and more preferably at least 4% wt. We also prefer the organic liquid to have a low volatility under stripper-reactor overhead conditions, such that carry over of the preformer organic into the cobalt absorber s kept to a minimum. Typically a product alcohol is used as the organic liquid, but we prefer to use a hydrogenation product because the use of this as the organic liquid in the preformer reduces the hydraulic and energetic load in the alcohol distillation section. The alcohol contained in the organic preformer liquid preferably but not necessarily has the same carbon number of the alcohol produced in the hydroformylation reaction. We prefer to use an alcohol having at least 8 carbon atoms, more preferably at least 9 carbon atoms on average. The sulphur may thus build up in this fully closed loop system, and the sulphate in the water to the preformer may for example reach levels of up to 6000 ppm of sulphur, mainly present as $CoSO_4$. Because this cobalt species is inactive in the preformer and does not form cobalt carbonyls, it is desirable to monitor sulphur in the preforming feed closely, and avoid its build-up to a level above 5000 ppm wt of sulphate, preferably not more than 4000 ppm wt, more preferably at most 2000 ppm wt and most preferably 1000 ppm wt.

When the Cobalt Flash technique is operating in "Cobalt Flash" mode, the organic stream over the preformer reactor does not form a closed loop, but eventually leaves the process with the organic hydroformylation reaction product after cobalt removal. We have found that in this operating mode, more sulphur may leave the system with the organic product than what enters the system, and the sulphur level in the closed loop water system may reduce. This operating mode may therefore act as a sulphur purge from a previous build-up. The sulphur levels in the Cobalt Flash system may thus be controlled by timely shifting from "demet" mode to "Cobalt Flash" mode. This method of alternating operating mode may be used to move some or all of the sulphur, which would end up in the light oxonation fraction (LOF) byproduct of one alcohol grade, into the LOF byproduct of another alcohol grade.

The sulphur present in the hydroformylation process typically ends up for a major part in the LOF, which may be separated off from the product aldehyde or, when a sulphur resistant hydrogenation catalyst is used for the hydrogenation, after any hydrogenation of the aldehydes to the alcohol. Only a very minor part may then end up in the alcohol product stream and in the heavy oxonation fraction (HOF).

In a multi-grade alcohol plant using the suitable decobalting technique, part of the sulphur present in the feedstock of a lighter grade oxygenate, for example present at a level of 20 ppm, may therefore end up in the LOF byproduct of a heavier grade alcohol. This may also be a method to reduce the sulphur in C6 or C7 alcohols made from pentene or hexene feedstocks containing significant levels of sulphur.

We have found that the Cobalt Flash process requires the use of particularly selected construction materials in specific parts of the process, in particular where water and acid may be present. The stripper-reactor is preferably filled with a packing, which may be structured or non-structured. We prefer to use a non-structured packing because it is less prone to fouling. Important for the stripper-reactor operation are the oil-water interface and the liquid residence times. We have found that the stripper-reactor is typically oil-water mass transfer limited, and not gas-liquid mass transfer limited. These stripper-reactor internals provide a large metal surface exposed to the acid solution under reducing atmosphere, and we prefer to use a particularly high quality corrosion resistant metal for this packing, such as alloy C276 or equivalent, and for the other internals alloy 904L or equivalent austenitic stainless steel. If the cobalt water concentration step as part of a Cobalt Flash process is performed in an evaporator, we have found that in particular the reboiler, the pump-around and the overhead systems thereof are susceptible to corrosion, especially in the presence of chlorine and at the location where boiling or condensation starts. Chlorine may come in with e.g. octene feeds coming from a Dimersol X process, at levels of about 10 ppm by weight. We have unexpectedly found that in the oxidizing evaporator system duplex stainless steels and nickel based alloy 625 are acceptable materials of construction in this evaporator service, preferably with chlorine levels of at most 10 ppm by weight in the water streams. We have also found that the feed system to the preforming reactor, particularly from the location the syngas is injected and even more particularly the first preformer reactor inlet, requires particularly corrosion resistant materials. The reactor vessel itself is preferably made of duplex stainless steel alloy 2205 or equivalent. We prefer to use nickel based alloy C276 or equivalent for all preforming feed equipment in contact with the reducing vapour phase and liquid of the process streams, such as the feed piping and the first reactor inlet or top head. Catalyst retaining mesh screens are preferably made from a material that is more resistant than the material they are in contact with. The mesh screen at the inlet of the first preformer reactor is preferably also made of alloy C276, while SS 316 was found to be suitable for the outlet mesh screen in the same reactor. The closure gasket, typically requiring a different hardness and corrosion resistance than the vessel shell, is preferably made of alloy 725 or equivalent. We also prefer to apply a special welding procedure during assembly of this equipment, particularly on the heavy wall duplex stainless steel, which consists essentially of specific welding procedure specifications and procedure qualification, including mechanical and corrosion testing. The welding parameters, such as heat input and welding fillers composition are controlled to obtain sufficient corrosion resistant welds, free of detrimental phases in the heavy wall duplex stainless steel equipment.

The evaporator is preferably designed for fouling service. We prefer to provide a single stage flash having a high liquid circulation rate over the reboiler. We prefer to use duplex stainless steels and alloy 625 as the construction materials for such oxidizing system.

We have found that over time, in the closed loop water cycle of a Cobalt Flash technique, metals other than cobalt may also build up, particularly from corrosion of equipment surfaces. Such metals may be for example Fe, Cr, and Ni. In order to control the levels of such components before they may negatively affect the process, we prefer to withdraw a part of the water present in the system, preferably from the evaporator feed. We prefer to recover the metals from such a stream before discarding. For that purpose we prefer to first raise the pH of the stream to at least 10, such as by the addition of caustic soda, such that all the metals convert to their hydroxides and the hydroxides of most metals, such as Co, Fe, Cr and Ni, come out of solution. The stream may now be filtered, and we prefer to use a cross-flow filter system for that purpose. Suitable filter systems may contain ceramic membrane filters and may be obtainable as CeraMem® filter modules, available from HPD, a Veolia Water Solutions and Technologies company. We have found that particles down to 0.2 micrometer may successfully be filtered out, and that the permeate may readily be disposed of in a regular plant waste water system, preferably after lowering the pH down to the range 8-10 by e.g. the injection of $CO_2$ which offers the advantage of being auto-controlling the pH to at most 9 due to the buffering effect. The retentate is a viscous paste containing for example 3-20% wt solids from almost all of the heavier metal hydroxides. Thanks to its low volume, this may be easily disposed of in an environmentally friendly way or used for recovery of the metals therein.

We have also found that fouling in the Cobalt Flash stripper-reactor may be minimised. We have found that when the main cobalt-containing feed streams to the stripper reactor are introduced above the packing, at the top of the tower, that cobalt deposition in the overhead system is significantly reduced. We also prefer to provide a static mixture in the feed line in order to ensure intimate water/oil mixing. We also prefer to avoid splashing of liquid from the feed nozzle, as evaporation of splashed droplets may cause precipitation and solids formation in the tower top and overhead system. We have also found that introduction of an amine into the stripper-reactor, such as may occasionally be entrained with the syngas feed from an upstream step using an amine for $CO_2$ absorption, is preferably minimised if not avoided because of the stripper-reactor fouling it may cause.

The Cobalt Flash stripper reactor is provided with a reboiler at the bottom, and also with an injection point for the stripping gas. We prefer to provide a thermosyphon type reboiler and to inject the stripping gas into the bottom of the reboiler, such that the gas-lift effect adds to the thermosyphon effect and provides additional driving force for liquid circulation from the stripper-reactor bottom to the reboiler and back. Such a system has been found to be very quick in start up.

The combination of Cobalt Flash with a two-step demetalling process combining carbonyl extraction with a further airless or air demet step also provides suitable offgas streams for applying the treatment step according to the invention, and also provides for a suitable embodiment according to the current invention. The combination with air demet is described in more detail in copending application under attorney docket number 2008EM222.

In a Cobalt Flash environment, high pressure and/or intermediate pressure offgasses may be separated that contain volatile carbonyls, and which may be advantageously be removed therefrom in order to protect a gas recycle compressor from fouling. The removal is preferably performed at a higher pressure, in order to preserve the energy efficiency in the gas recycling. It may therefore not be desirable to let the offgas down in pressure to the Cobalt Flash absorber tower, wherein a major portion of the cobalt is absorbed into olefin feed or another suitable organic absorbent for direct recycle as an organic carbonyl solution to the hydroformylation reaction. The amount of cobalt to be removed from these offgasses may be too small to justify a separate high pressure absorber combined with the necessary high pressure pumps for routing the cobalt-containing olefin or other organic liquid directly to the hydroformylation reaction. The more economic solution for protecting a gas recycle compressor while recovering the cobalt as part of the cobalt catalyst cycle may therefore be to apply the process according to the current invention to one or more of the intermediate and high pressure offgasses as part of the Cobalt Flash process. The invention therefore provides for a process wherein the demetalling step comprises a "Cobalt Flash" decobalting and recycling system.

The Cobalt Flash technique includes a concentration step on the $Co^{2+}$ solution before routing this to the hydroformylation reaction or to the preforming reactor. The concentration step, such as an evaporator, produces a byproduct water stream that contains little or no $Co^{2+}$, and which may also contain some of the acid that is present in the upstream stripper-reactor. This byproduct water stream is typically used at least partly for washing the organic cobalt-depleted reaction product (3) for removal of last traces of cobalt. We have found that the feed stream, to the concentration step is a suitable aqueous absorption liquid for treating intermediate and/or low pressure offgasses according to the current invention, and we prefer to recycle part of this feed stream for that purpose.

We have found that when an oxo process comprising a preforming reactor containing a heterogeneous preforming catalyst needs to be stopped, even for as short as a few hours, it is preferable to flush the preformer reactor with a stream that contains little to no cobalt so that any reaction, particularly the cobalt plating reaction (3), is stopped and the catalyst is not affected or the reactor plugged before the restart. We have found that the evaporator overhead stream is particularly suitable to flush the preformer from cobalt during a shutdown or even a temporary process squat. This also avoids that a methanation or Fischer-Tropsch condensation reaction would start in the preformer reactor, which could lead to a possible temperature runaway. We have found it also advantageous to always provide a liquid feed to the preformer reactor when feed gas is provided, as it provides a heat sink.

In such an oxo process comprising a preformer reactor, we prefer to provide a lead guard bed to the preformer reactor zone, filled with a solid adsorbent material with preferably a high surface area, such as pumice, so that any metal present, but which may also form under the preforming conditions of temperature and hydrogen partial pressure, may deposit on the adsorbent and not reach the preforming catalyst. Corrosion products, such as dissolved Cr, may deposit in such a guard bed. We prefer to provide this guard bed in a separate vessel that may be taken out of service independently from the preformer reactor, such that its content may be replaced or regenerated while the remainder of the process continues running. We also prefer to provide two catalyst-containing preforming reactor zones, either in parallel or in series, such that a catalyst replacement may be performed without a full process shutdown. We prefer to provide a preforming reactor with an L/D ratio of at least 60, typically about 70, and containing two beds in series, avoiding the need for internal redistribution between the beds.

We prefer to use a palladium catalyst in the preforming reactor. Suitable catalysts are disclosed in U.S. Pat. Nos. 5,321,168, 5,434,318 and in particular U.S. Pat. No. 5,600,031. The palladium loading may be in the range of 0.1 to 5% by weight, based on the total weight of the dried catalyst. Typically the catalyst activity is proportional to the metal loading. On the other hand, palladium is rather precious and costly, making the catalyst with a higher loading more expensive. Higher metal loadings may also lead to more clustering of the palladium, thereby loosing some of the gains of the higher metal loadings. We therefore prefer to use palladium loadings of at most 3% by weight, more preferably at most 2.5% by weight. Our preferred catalyst contains from 1.8 to 2.2% by weight, and typically 2% by weight of palladium.

Also for activity reasons, we preferably have good nanoscale homogeneity of the active metal, meaning no clustering of the palladium on a nanometer or a transmission electron microscopy (TEM) scale, with little to no islands of metal clusters. For this purpose, we prefer that the average distance between the metal particles is larger than 2 times the average diameter of the particles, more preferably larger than 4 times the average diameter. We also prefer to use metal precursors other than metal chlorides, such as nitrates, but more preferably organic precursors, such as oxalates, acetates, succinates or amines, because this reduces the risk of having residual chloride on the catalyst, which otherwise may leach into the process streams and lead to corrosion. We also expect that by providing a small amount of a second metal, such as 5-10% by weight and based on the weight of palladium, preferably of platinum, the stability of the catalyst activity may be improved, most probably because it reduces the tendency of the palladium particles for clustering.

We prefer to use so-called coated or shell-type catalyst, i.e. catalysts that have the palladium located towards the outside of the catalyst particles, such as described in U.S. Pat. No. 5,600,031 and CA 2,612,435, e.g. with all or at least 80% of the metal in an eggshell-type zone in the catalyst particles from the outer surface up to a penetration depth of at most 200 micrometer ($\mu m$), more preferably at most 150 $\mu m$, even more preferably at most 100 $\mu m$ as stated in U.S. Pat. No. 5,600,031.

As support for the catalyst, we prefer to use a support that provides an average pore diameter of at least 3 nm (30 Angstrom), preferably at least 4 nm and more preferably at least 5 nm. We like to use extrudates as catalyst particles, because of the lower pressure drop as compared to flakes, but spheres would also be suitable. We prefer to use extrudates having a quadrilobe shape. The support for this catalyst preferably has large pore dimensions, but this comes at the expense of particle crushing strength and surface area. The average nominal diameter of our extrudates may be 3 mm, and is preferably at least 1 mm, more preferably at least 1.3 mm, even more preferably at least 2 mm and yet more preferably at least 2.5 mm.

The average side crushing strength of our catalyst extrudates is preferably at least 10 N/mm, more preferably at least 12 N/mm with no more than 10% of the particles having less than 8 N/mm. Even more preferably the average side crushing strength of the extrudates is above 17.8 N/mm (4 lb force/mm) and yet more preferably above 22 N/mm (5 lb force/mm).

We prefer to select activated carbon in or as the support, and we prefer to use carbon which has a surface area, measured according to the BET method, in the range of 800-1000 $m^2/g$, preferably around 900 $m^2/g$. The higher particle crushing strength offers the advantage of sustaining the higher pressure drop caused by the high L/D ratio of the reactor design. We have found that this reduces the amount of dust and/or chips formed during operation of the catalyst, but also during catalyst handling. We also prefer that the final catalyst is making less than 1% wt of catalyst fines smaller than 0.3 mm when it is exposed in a bulk crush strength measurement to a force of 6.9 barg (100 psig).

We prefer to operate the preformer with a CO partial pressure of at least 90 bar, preferably at least 110 bar and more preferably at least 120 bar. We have also found that it is advantageous in a Cobalt Flash process to cool the preformer outlet as soon as possible to a temperature of at most 100° C., preferably at most 70° C., more preferably at most 60° C. and typically in the range of 45-55° C., and before entering the stripper-reactor, such that the stripper-reactor inlet mixture may be at a temperature of at most 65° C., because this reduces the occurrence of disproportionation of cobalt carbonyls upstream of the stripper-reactor and improves the efficiency of the stripper-reactor in removing more cobalt as volatile cobalt carbonyl. We have found that good control of the catalyst cycle operation and thus the hydroformylation process depends on good monitoring of the content and type of cobalt in a variety of process streams. We have found that X-ray fluorescence is a suitable technique, and we have found that it may be applied on-line, and even in the form of a multi-stream on-line cobalt analyser. Such a monitoring technique is particularly helpful in the operation of a complex catalyst cycle having multiple steps, in particular any of the cycles according to the Cobalt Flash technique.

The stripping gas in the Cobalt Flash technique preferably forms a closed loop from the stripper-reactor tower to the absorber tower and back, driven by a low-head compressor or blower. When olefin feed is used in the absorber tower, a portion may evaporate, be carried to the stripper-reactor, absorb in the oxo product and leave the hydroformylation process unreacted. We prefer to minimise this undesirable bypass by chilling the gas from the absorber to a temperature of at most 15° C., thereby condensing as much as possible of the vaporised feed olefins, before returning the gas to the stripper-reactor tower bottom. We also prefer to chill the olefin feed to the absorber tower to a similar temperature, as we have found that this reduces the production of an amorphous cobalt-containing precipitate in the absorber, which may cause plugging of filters in the feed system to the hydroformylation reaction.

The techniques of the present invention may be used in the cobalt catalysed hydroformylation reactions as described in WO 2005/058787. The products of such a cobalt catalysed reaction include aldehydes, alcohols, formate esters, acetals, ethers, ether-alcohols, as well as unreacted olefins and paraffins. The cobalt depleted organic reaction products can be hydrogenated to produce high purity alcohols. A preferred hydrogenation reaction is described in WO 2005/058782. Alternatively the aldehydes may be optionally purified and oxidised to produce an acid, using conventional oxidation techniques. The high purity alcohols may then be used for example in the production of plasticiser esters and synthetic lubricants. Preferred esterification reactions are described in WO 2005/021482, WO 2006/125670 and in our copending patent applications PCT/EP2008/001837, which published as WO 2008/110305 and PCT/EP2008/001838, which published as WO 2008/110306 respectively. Also the acids may be esterified with an alcohol to form an ester. If the alcohol is a polyol, a polyol ester is typically produced. Optionally, not all of the hydroxyl functions are esterified, and free alcohol functions may remain present in the polyol ester, such as from 5 to 35% relative to the starting alcohol functions in the polyol. These polyol esters may also find use as synthetic lubricants. Further esters of commercial interest may be made by esterification of the high purity alcohols made according to the invention with an acid or anhydride. The acid or anhydride preferably is selected from the group consisting of adipic acid, benzoic acid, cyclohexanoic acid, phthalic acid, cyclohexanoic dicarboxylic acid, trimellitic acid, or any of their anhydrides, or mixtures thereof.

In a further embodiment the aldehyde containing materials may be purified to isolate the aldehydes, and these may be oxidised to produce carboxylic acids, which may be used in the production of synthetic esters, which in their turn may be used as lubricants. Alternatively, the acids may be used in the production of metal salts, which find use as additives in a wide range of applications.

In an embodiment, the invention therefore provides a process further comprising hydrogenating the reaction product (3) and recovering an alcohol product from the hydrogenation product. The alcohol product may contain from 6 to 13 carbon atoms, such as from 7 to 11 or from 8 to 10, such as 9 carbon atoms. The alcohol product may be an alcohol mixture, and this mixture may have an average carbon number of from 6 to 15 carbon atoms, such as an average carbon number between 8 to 13, such as between 8.5 and 10.5 or between 8.5 and 9.5.

In another embodiment, the invention provides for a process further comprising esterifying the alcohol product or product mixture with an acid or anhydride to form an ester. The acid or anhydride is preferably selected from the group consisting of benzoic acid, phthalic acid, adipic acid, trimellitic acid, cyclohexanoic acid, cyclohexanoic dibasic acid, pyromellitic acid and their anhydrides. Particularly the phthalate esters are of significant commercial importance.

The ester molecules produced using the process of the invention may comprise aromatic rings, such as alkyl benzoates, di-alkyl phthalates or tri-alkyl trimellitates. The aromatic rings in these ester molecules may be hydrogenated to produce the corresponding cyclohexane equivalents, such as mono-alkyl, di-alkyl or tri-alkyl cyclohexanoates. In particular, di-isononyl phthalate (DINP) may be further hydrogenated to form di-isononyl cyclohexanoate. The process of the invention may therefore be for the production of a phthalate di-ester, in particular DINP, and further comprise the hydrogenation of the phthalate di-ester to the corresponding cyclohexanoate, in particular di-isononyl cyclohexanoate. Suitable hydrogenation processes are disclosed in EP 1 042 273, US 2004/0260113, US 2006/0149097, US 2006/0166809 or WO 2004/046078.

In yet another embodiment, the invention provides a process wherein the ester is a phthalate and further comprising the hydrogenation of the phthalate ester to a hexahydrophthalate ester.

The olefinic material that is hydroformylated may be short or long chained compounds containing olefinic unsaturation, depending on the final product desired. Most organic compounds possessing at least one non-aromatic carbon-carbon double bond may be reacted by this method. Generally the compound will have at least five carbon atoms. Thus, straight and branched-chain olefins such as pentenes, hexenes, heptenes, octenes, nonenes, decenes, undecenes, dodecenes, tridecenes and tetradecenes, styrene, olefin oligomers such as di- and tri-isobutylene and hexene and heptene dimers, olefinic fractions from the hydrocarbon synthesis process, thermal or catalytic cracking operations, and other sources of hydrocarbon fractions containing olefins, and mixtures of all of these, may be used as starting material, depending upon the nature of the final product desired. The feed may include a mixture of isomers, both skeletal and in double bond location or it may be isomerically pure (or nearly so) skeletally and/or in double bond location.

In a preferred embodiment, the olefinic material is a mixture of olefins having a carbon number of from $C_5$ to $C_{18}$, more preferably $C_6$ to $C_{15}$. It will be recognized that the olefin feed may not consist of 100% olefins, nor of 100% olefins within the specified carbon number range, but may be a distribution of olefins having different carbon chain lengths. In a particularly preferred version of this embodiment at least 50 wt. %, preferably 70 wt. %, more preferably 80 wt. %, still more preferably 90 wt. % of olefins are in the specified carbon number range. In certain cases it may be preferable to use a feed of 100 wt. % (or nearly so) of the specified carbon number or carbon number range.

In another preferred embodiment, the olefinic material is the olefinic reaction product of the acid catalyzed oligomerisation of lower olefins, preferably propylene and/or butenes, which may also optionally also include pentenes. Ethylene may be present in minor quantities during oligomerisation, as well as trace quantities of dienes or acetylenes such as butadiene, methyl acetylene, propadiene or pentadienes. Heavier olefins may be added to the feed, preferably selectively separated and recycled from the oligomerisation product, to selectively increase the production of selected carbon number products.

In yet another preferred embodiment, the olefinic material is the olefinic reaction product of the oligomerisation of various lower olefins and compounds having olefinic unsaturation, using regular or surface deactivated zeolite catalysts such as those described in U.S. Pat. Nos. 3,960,978; 4,021,502; 4,076,842; 4,150,062; 4,211,640; 4,520,221; 4,522,929; 4,524,232; 4,547,613; 4,568,786; 4,855,527; 4,870,038; 5,026,933; 5,112,519; 5,245,072; 5,417,869; 5,985,804; and 6,013,851.

Even more preferred as olefinic material used as feed in the present invention are $C_6$ to $C_{26}$ olefins containing the required olefin or olefins within the $C_5$ to $C_{14}$ range, such as comprising $C_8$ to $C_{26}$ olefins, more preferably $C_8$ to $C_{23}$ olefins, most preferably $C_8$ to $C_{18}$ olefins, conveniently prepared by contacting lower olefins under polymerization conditions with siliceous mono-dimensional acidic zeolites such as ZSM-22 and ZSM-23 zeolite having pore activity and wherein the zeolite surface is rendered substantially inactive for acidic reactions.

By "lower olefins" or "lower olefinic material" as used herein is simply meant that the starting material to be oligomerised over the zeolite has lower carbon numbers than the final product. The oligomers may be dimers, trimers, tetramers or higher oligomers, or mixtures thereof. It is preferred that the starting material is a $C_3$ or greater olefin (or mixtures thereof), and in a preferred embodiment the olefinic material supplied to the oxonation reactor(s) according to the present invention derive from the oligomerisation of $C_3$ and/or $C_4$ olefins using the aforementioned modified zeolites. In a particularly preferred embodiment, a feed is used comprising butenes (more preferably n-butene) and propylene in the ratio of about 1:0.01 to 1:0.049 wt %. Conveniently, paraffins are also present in the feed to act as a heat sink in the reaction. The amount of paraffins to use to provide a desired heat sink function can be readily determined by one of ordinary skill in the art.

In another embodiment the process of the invention uses LAOs and/or LIOs (linear alpha olefins and linear internal olefins, respectively), which terms are well-known in the art, as olefinic material.

Other olefinic materials that may be used as a feed into the oxonation or hydroformylation reactors include oligomers produced by the Octol® process or the Dimersol® process. See, for instance, the previously mentioned U.S. Pat. No. 6,015,928. Octol® and Dimersol® are registered trademarks owned respectively by Degussa and Institut Francais du Pétrole (IFP). Other preferred olefinic materials may be made using the process as described in U.S. Pat. No. 6,437,170. Yet other olefinic materials include oligomers produced using solid phosphoric acid (SPA) catalysts and those produced using ZSM-5, ZSM-57 and/or SAPO-11 catalysts, procedures which are known in the art. Other olefinic materials may be produced using oligomerisation processes as disclosed in WO 2006/133908, WO 2006/133967 or WO 2007/006398.

An alternative feed to any of the oligomerisation processes mentioned comprises 0.1-20% wt isoolefin, particularly isobutylene and/or isoamylene, more preferably wherein the content of the isobutylene and/or isoamylene is from 0.5-5.0% wt. A preferred source of such a feed is the unreacted effluent from a methyl tertiary butyl ether (MTBE) unit. Another preferred source is the heavier byproduct stream of an oxygenate-to-olefins process, which may be rich in C4 and C5 olefins, up to 85 or 90% wt $C_4$+$C_5$, and typically only being 1-5% branched, but may in addition also contain some $C_3$ and possibly also some $C_6$ compounds, again mainly olefinic.

Typical hydroformylation reaction conditions include a temperature of about 125° C. to about 200° C. and/or a pressure of about 100 bar to about 350 bar, and/or a catalyst to olefin ratio of about 1:10000 to about 1:1. The molar ratio of hydrogen to carbon monoxide is conveniently in the range of about 1 to about 10. The process may also be carried out in the presence of an inert solvent such as a ketone, e.g., acetone, or an aromatic compound such as benzene, toluene or xylenes.

Any type of hydroformylation reactor may be operated in combination with the present invention, although those reactors are preferred that are more tolerant to the presence of a free water phase. Suitable hydroformylation reaction systems are described e.g. in U.S. Pat. Nos. 3,830,846, US 6,444,856, US 6,642,420, US 6,723,884, US 4,320,237, US 6,720,457 and US 6,015,928. A particularly suitable hydroformylation reactor is described in WO 2008/051301.

We have found that the loop reactors disclosed in some of these documents may be significantly improved, giving them a higher capacity, increasing the allowable cobalt loading and providing a smoother operation. The loop reactors typically consist of one pipe as the riser leg and a second pipe forming the downcomer leg, the legs being connected at top and bottom with a top and bottom bend. The riser and downcomer legs are typically provided with a jacket for temperature control and heat removal, and a heat exchanger is typically provided as part of the downcomer leg, usually in its lower half, for further heat removal. The heat exchanger is typically of the shell and tube type, and called a conditioner. In a series of loop reactors, the last reactor may not need a conditioner as the heat generated in such reactor is lower. Because of the lower heat generation, the back-end reactor in a series of hydroformylation reactors may preferably be of a different design, such as a vertical tank reactor only containing internals for providing an internal gas-lift and/or without internal cooling coils.

The conditioner in a loop reactor is typically of a larger diameter than the downcomer pipe, and is connected thereto by means of a top cone and a bottom cone. The bottom bend of a reactor is typically provided with a vertical inlet nozzle located tangential underneath the riser leg, and the top bend is typically provided with an outlet nozzle located at the top point of the bend. We prefer that the downcomer leg has a smaller diameter than the riser leg, such that liquid velocity is higher and downward entrainment of gas bubbles is increased in the downcomer leg. The bends are then adapted to connect to the two legs having a different diameter.

The cone on top of the conditioner is preferably of the diffuser type, having a small wall angle relative to the cone axis, preferably less than 15°, typically about 9°, so that reverse flow is minimised or avoided, in particular near the outlet of the cone where the reaction mixture enters the tubes of the conditioner. We prefer to provide venturi funnels at the inlet and the outlet of the conditioner tubes, such that flow differences between different tubes are reduced. We prefer to provide a few, for example four, conditioner tubes without a venturi funnel at the top, to allow more complete draining of liquid from the reactor when it is emptied.

We prefer to equip a typical loop reactor with five or more thermocouples for measuring the temperature of the reacting mixture at various locations. The more important temperatures to be measured are the reactor outlet temperature and the temperature at the top of the conditioner typically as the highest temperature point. The difference between these two temperatures provides a measure of the circulation rate inside the loop reactor. Other temperatures of interest to measure include the temperatures at the feed mixing point, halfway up the riser leg, and at the conditioner outlet.

We have found that the improved loop reactors may provide an increased internal reactor volume, such as e.g. 7.5 $m^3$ relative to the standard of about 5 $m^3$. We have found that internal reactor volumes up to 12 m3 are achievable, above which it becomes more difficult to fabricate the loop reactor bends and find seal rings of appropriate size. We have found that the temperature and velocity profiles over these reactors are more uniform and that these reactors are easier to start up and shut down, that back mixing and stagnant zones are substantially eliminated, and that the reactors are less sensitive to process upsets. We prefer to use Duplex stainless steel for the parts of the reactor in contact with the process fluid, for its better corrosion resistance combined with the advantages of its higher strength, allowing smaller wall thicknesses and thus better heat transfer.

We have also found that an oxo plant using these improved loop reactors may be started up faster and with fewer problems than plants with other forms of reactor. For start-up we prefer to fill the reactors with an inert liquid, such as the light oxonation fraction (LOF) byproduct from alcohol distillation. Syngas is then be introduced in order to start the gas-lift driven liquid circulation, upon which also the cobalt-containing olefin feed is introduced. We have found that a fast and high heat input to the lead reactor, e.g. via the conditioner or the jacketing system by means such as by direct steam injection, preferably of high pressure steam, after olefin feed introduction during a start-up may shorten the start-up time significantly.

We have further found that the operating stability of a lead loop reactor in a series of reactors, in particular the improved reactor as described, may be improved by feeding part of the olefin feed and/or part of the syngas feed to the reactor in second position. We have found that such a feed split may also bring extra capacity while maintaining lead reactor stability.

We have found that water has a beneficial selectivity effect on the hydroformylation reaction. However, the reactor design may not accommodate a free water phase, so the amount of water present may need to stay below the solubility limit of the organic phase. When the oxo reaction proceeds, the organic reaction mixture contains more oxygenates and the water solubility increases, in particular when alcohol is also formed. In a process comprising multiple hydroformylation reactors in series, we therefore prefer to inject water into a plurality of reactors, such as in the lead reactor and into the reactor in second position. The amount of water injected is preferably adjusted to the water solubility limit in the various process locations, and is also a function of the carbon number of the olefin feed and alcohol product.

We have also found that pressure control is important in operating a hydroformylation reaction. We have found it advantageous to control the syngas supply pressure to the hydroformylation reactor by controlling the inlet pressure to the high pressure (HP) compressors. This allows the reactor pressure to be kept as high as possible. We have found that this control is preferably done by controlling a recycle flow of intermediate pressure (IP) offgas from downstream to the HP compressor. This IP offgas is separated from hydroformylation reactor product, optionally but preferentially after cooling the reactor product, separating excess gas from the reactor outlet in a high pressure separator, and letting the liquid from this separator down to a lower pressure. This pressure let down may also be done in a plurality of steps, and each step may then result in an IP offgas, usually at different pressures. These offgasses will have different compositions, due to differences in vapour/liquid equilibriums for the individual stream components. Depending on their composition, there may be preferences for purging one or a selection of those streams, if only partially, and preferably recycling more of the other offgas stream or streams. In many cases it is more desirable to purge IP offgasses than HP offgasses, to control the build-up of inerts in the gas system around hydroformylation. This is particularly true for control of inerts such as methane and carbon dioxide, but may be less desirable to control nitrogen. Suitable purge and recycle schemes are also disclosed in WO 2005/058787, which is hereby incorporated herein.

The crude aldehyde-containing hydroformylation reaction product produced by the process of the invention, optionally after washing in a counter current water wash tower for removing traces of catalyst and remaining acid from the demetalling step, but preferably without such a washing step, is typically hydrogenated to produce a so-called hydro product. Typically such hydrogenation employs a heterogeneous catalyst and many types of catalysts are suitable. Upstream of the hydrogenation catalyst, we prefer to provide an additional adsorption step to remove the last traces of cobalt that may be left over in the hydroformylation product. More details may be found in US 2006/0129004. Passing the hydrogenation feed over an adsorbent, such as a bed of pumice or spent catalyst or any other suitable solid support, preferably already at hydrogenation reaction conditions and in the presence of hydrogen, we have found is most effective in protecting the hydrogenation catalyst from cobalt deposits. WO 2005/058782 discloses suitable hydrogenation catalysts and processes, as well as conditions that are suitable for operating the pumice filters. In addition, we have found a sulphided cobalt/molybdenum catalyst to be particularly suitable in this hydrogenation service. Also particularly suitable are the reduced nickel-molybdenum catalysts, e.g. carried on alumina support, that are disclosed in X. Wang et al, "Characterization of Active Sites over Reduced Ni—Mo/$Al_2O_3$ Catalysts for Hydrogenation of Linear Aldehydes", J. Phys. Chem. B 2005, 109, 1882-1890, which catalysts we have found are also suitable for hydrogenation for branched aldehydes. These catalysts preferably contain no, or only small amounts of phosphorus, such as 0-1.0% wt P, more preferably 0-0.5% wt P, as disclosed in U.S. Pat. No. 5,382,715. Most preferably they are substantially free of phosphorus, as disclosed in U.S. Pat. No. 5,399,793.

It is known that water improves the hydrogenation step, as it helps to convert formate esters and/or acetals to desirable product alcohol. We have found that acidic cobalt removal steps will produce hydroformylation reaction product streams that contain more acetals, and thus require more water when hydrogenated to produce an alcohol. Also when the hydroformylation reaction is operated with a higher conversion, the product will contain more formate ester and acetal byproducts, and the hydrogenation step may require more water.

Many types of fixed bed reactors are suitable for hydrogenation services. Tubular reactors are particularly suitable because of their temperature control advantages, but adiabatic chamber reactors may also be used. Such chamber reactors may contain a plurality of beds, and bed temperatures may be controlled by interbed quench, either by cooled recycle liquid or cooled hydrogen injection, fresh and/or recycled, into quench zones in between catalyst beds. It is preferred to mix the colder quench with the hot bed effluent well before entering the downstream bed. Therefore distributors and/or quench boxes may be provided. However, these reactor internals may impair easy catalyst unloading when it is deactivated, and/or make the loading of fresh catalyst more difficult. We have found it advantageous to provide a special reactor internal, called a removable quench box, such that it is readily removed during a catalyst change out and replaced afterwards. For more details about suitable hydrogenation reactors and their internals, we refer to copending application PCT/EP2008/053783, which published as WO 2008/128852. We prefer to use a partial recycle of hydrogenation product over the hydrogenation reaction in order to dilute the aldehyde concentration and reduce the temperature increase to below 30 degrees C., preferably in the range of 20-25 degrees C. We prefer to use recycle rates of 3-5:1. This may be achieved by hydrogenation product recycle or by interreactor product recycle when multiple reactors are used in series. We prefer to use interreactor product recycle, and operate at least the last hydrogenation reactor in the series in plug-flow mode, without recycle, in order to benefit of the higher conversion that may be achieved.

When the hydrogenation reaction is performed in multiple stages in series, optionally with interreactor product recycle over the first stage which may comprise two lead reactors in parallel, optionally followed by another two reactors in parallel, we prefer to direct the offgas that is separated at an interreactor gas/liquid separator to the second hydrogenation stage, as this reduces the overall hydrogen requirement while improving the hydraulics in the downstream hydrogenation stage. We have found that when the offgas is directed to the downstream hydrogenation stage, the gas/liquid separator may be operated with a minimum of instrumentation only protecting the liquid recycle pump from excessive gas and thus from cavitation. We have also found that injection of inert gas into the second hydrogenation stage may improve the reactor hydraulics, such as explained in WO 2006/086067.

When a sulphided hydrogenation catalyst, such as cobalt/molybdenum or nickel/molybdenum, is used, it may be pre-sulphided and activated before loading and loaded in a fully active state; or it may be pretreated with a sulphiding agent and activated in situ after loading into the reactor; or it may be loaded as an oxide precursor and be sulphided and/or reduced in situ. We prefer to sulphide the metal oxide catalyst precursor in situ at temperatures up to 332-337° C. (630-640° F.) and/or at low pressures such as 450–800 kPa (50-100 psig), and using a sour gas such as a mixture containing hydrogen and at least one sulphur component such as $H_2S$, DMDS and/or a DMDS decomposition product. However, these conditions may differ for different mixed metal oxide catalysts, e.g. Ni/W is easier to sulphide than Ni/Mo, and Co/Mo is in between. More details may be found in the disclosure by X. Wang already mentioned.

The hydrogenation reaction converts aldehydes, acetals, formate esters and acids into alcohols. The reaction typically takes place at 160-200° C. and at a hydrogen partial pressure of at least 30 bar, preferably at least 50 bar, and more preferably in the range of 70-100 bar. Generally the conditions in the hydrogenation section are such that traces of aldehydes and formate esters are left behind in the hydrogenation product. Where this is possible, such as with mixtures having a limited number of isomers, or single isomer alcohols, these traces may be distilled from the product alcohol in the distillation section that separates the product alcohol from the hydrogenation product. Such a distillation unit typically comprises distillation towers lined up in a 2-tower heart cut formation where the product alcohol is taken as overhead of the second tower. However, this is not preferred because of the loss of some of the product alcohol in the byproduct streams that is typically associated with such distillation operation.

We therefore prefer to provide an extra so-called hydrofinishing step on the distilled alcohol stream, to convert also most of the remaining traces of aldehydes and formate esters in this stream.

Many hydrogenation catalysts are suitable for hydrofinishing service, and we prefer a nickel catalyst because of its high activity and selectivity at mild conditions. We prefer a massive nickel catalyst containing typically about 50% wt Ni metal on a dry catalyst basis, and we prefer to operate at a pressure in the range of 20-40 bar gauge and at a temperature in the range of 80-110° C. The feed to the hydrofinishing unit may have a carbonyl number in the range of 0.2-0.8 mg KOH/g, and we prefer to introduce hydrogen at a rate that is typically about 6 or 7 Nm3 per ton of liquid feed to the unit. If the catalyst employed in the upstream hydrogenation is tolerant to sulphur, such as a sulphided catalyst described above, we prefer to also use a sulphur tolerant catalyst in hydrofinishing service. Our preference is to use sulphided Ni/Mo, at a pressure in the range of 45-70 bar gauge and a temperature in the range of 120-160° C. Based on a feed having a carbonyl number in the range of 0.2-0.8 mg KOH/g, we then prefer to use a hydrogen treat rate of about 15 Nm3/ton of liquid feed.

The operating conditions in hydrofinishing are generally a compromise between the promotion of the desired reactions that convert the aldehydes and formate esters, and the limitation or suppression of the side reactions producing lights and/or heavies, such as alcohol dehydration to olefins, possibly followed by olefin hydrogenation to paraffin, etherification of alcohols to di-alkyl ethers, esterification of trace acids with alcohols to di-alkyl esters plus water, etc. The hydrofinishing conditions are usually such that any lights and/or heavies made in hydrofinishing do not need to be removed from the product alcohol.

Trace aldehydes and formate esters may also be removed by treating the product of the hydrogenation step, or more preferably the alcohol product from the distillation step downstream thereof, with sodium borohydride (NaBH4). We prefer to preheat the product alcohol to a temperature of typically 80° C. and treat it in a vessel containing solid NaBH4 tablets. The alcohol may be recycled if needed to reach the target carbonyl number. We have found that the treatment effect is faster with lower molecular weight aldehydes, with increasing temperature and with offering a higher accessible tablet surface to the liquid. We prefer to treat the alcohol product from the distillation step to a carbonyl target between 0.05-0.15 mg KOH/g, as this avoids overtreatment, reduces the formation of free hydrogen, leaves essentially no residual NaBH4 behind, and delivers a product alcohol having a lower sodium content, which is important for some of the downstream processes, such as esterification. We have learned that in a NaBH4 treatment process using stoichiometric treatment levels, at least about 6% of the hydrogen atoms will end up as free hydrogen gas. Any overtreatment will typically almost fully convert to free hydrogen gas, and is preferably avoided.

Optionally an additional drying step may be provided to bring the water content in the product alcohol down, such as below the typical spec of 500 ppm wt. For safety reasons, dissolved hydrogen, left over from the hydrofinishing or the NaBH4 treatment step, is preferably removed before sending the product alcohol to tankage or into a shipping container. This may be achieved by any suitable means, such as by at least one and preferably multiple flashing steps, but we prefer to strip the product alcohol with a nitrogen stream, preferably a dry nitrogen stream, such that this stripping acts as a drying step because at the same time the water content is also reduced. We prefer to perform such nitrogen stripping at atmospheric pressure and at a temperature of about 70° C., using a nitrogen treat rate of about 1 m3 per ton of liquid product. Preferably a multi-stage tower is used to enhance the stripping effect of the nitrogen in the removal of hydrogen and/or water. Alternatively, nitrogen stripping can be effected by injecting nitrogen into product alcohol as it is loaded into a conveyance vessel such as a railcar, truck, or marine compartment.

An alternative means to provide hydrogen and water removal is by splash-loading of product alcohol into storage tanks. Splash-loading is achieved by filling the tanks from the top instead of from the bottom as is more customary. Splash-loading of higher alcohols may be considered safe because the product alcohols are not static accumulators. The use of two or more splash-loaded tanks in series can be used to improve hydrogen removal. Further, the removal of hydrogen may be further enhanced by the use of a liquid dispersion device such as a spray nozzle as the product alcohol is injected into the tanks.

Product alcohol may also be analyzed to verify whether hydrogen has been removed down to a safe concentration. For this purpose, we prefer to sample the alcohol into a container up to 75-90% filled. The container may then be shaken to achieve equilibrium of hydrogen between the liquid and vapor phases. A sample of the vapor phase may then be introduced into a gas chromatograph suitable to detect very low concentrations of hydrogen. The results of this analysis may then be used to assure that the product alcohol is safe for transport.

Many of the steps of the processes disclosed herein may consume hydrogen, in particular the hydroformylation step, any hydrogenation step, and the hydrofinishing step, if present. The hydroformylation reaction may be fed additional hydrogen for gas composition control, such as explained in WO 2005/058787. The hydrogen may be supplied from a variety of sources, such as but not limited to refinery processes, partial oxidation (POX) of various starting materials, steam reforming, autotheimal reforming (ATR) or the like. One of the potential sources of hydrogen is a refinery process called catalytic reforming, sometimes also called a Platforming process, wherein a refinery liquid stream, typically a naphtha or equivalent containing primarily naphthenes and/or paraffins in the C6 to C11 range, is converted to a product rich in aromatics over a heterogeneous precious metal chloride catalyst. These kind of processes are often known as a "Powerformer" or "Powerforming" processes (developed by Exxon), or as Continuous Catalyst Regeneration (CCR) processes (as e.g. offered by UOP and IFP). The hydrogen from such a catalytic reforming processes contains small amounts of chloride, at a level in the order of 1-10 ppm by volume. It is believed that most of this chloride is present as hydrogen chloride, which is more readily detected by direct gas analysis and at a typical level of 4-8 ppmv. It is however suspected that, in addition, also organic chlorides may be present, and possibly even at similar levels as the HCl. Many hydrogen consuming processes are sensitive to chloride poisoning, and a chloride removal step is typically foreseen to remove HCl from the catalytic reforming hydrogen byproduct, most typically down to a level of at most 1 ppmv. A typical chloride removal step is the adsorption of chloride over activated alumina, such as alumina 9139A from UOP, CI-750 and CI-760 from BASF, Alcoa 760 from Alcoa, Puraspec from Johnson Matthey, over ZnO such as members of the Süd-Chemie Actisorb Cl series, e.g. Cl 13, and/or over a molecular sieve, such as type CLR-454 obtainable from UOP or Unimol types from Unicat.

Some of the typical process steps in the production of the oxygenates, such as the alcohols, disclosed herein, may however be particularly sensitive to chloride poisoning, such as a copper chromite hydrogenation catalyst used for aldehyde hydrogenation. The alcohol production process may also employ a hydroformylation catalyst cycle comprising a closed loop with minimal purge, in particular an aqueous closed loop, such as with several of the techniques discussed herein and/or disclosed in our co-pending patent application U.S. Ser. No. 61/092,833. Organic chlorides may become again converted to HCl in these processes. The traces of chloride coming with the hydrogen from a source such as a catalytic reforming may therefore build up in any of these aqueous loops to levels where corrosion due to chloride may become problematic, and/or where the chloride acts as a poison to the chemistry of the hydroformylation catalyst cycle, such as in a preforming step. The hydrogen from the catalytic reforming unit as feed to the alcohol production process therefore may need to be cleaned up to a lower level of chloride than for other hydrogen consuming processes, preferably to a level of at most 0.1 ppmv and more preferably at most 0.02 ppmv of chloride. We have found that the catalytic reforming hydrogen may also contain organic chloride compounds, at a concentration up to for example 10 ppm volume. Further we have found that organic chloride compounds are more difficult to remove by adsorption on the conventional adsorbents. Organic chlorides may therefore more easily pass through the adsorbent bed and still may cause problems in the alcohol production process. In addition, an activated alumina adsorbent may also convert part of the HCl in the hydrogen to organic chloride compounds. The activated alumina may react with HCl to form $AlCl_3$. This $AlCl_3$ is a catalyst for the formation of organic chlorides, and also for polymerising trace olefins in the hydrogen stream to form heavier components, sometimes referred to as "green oil". Organic chlorides are more difficult to detect, and typically do not show on the conventional chloride analytical methods, such as the well known Dräger tube.

We have found that an alkali treated molecular sieve, more particularly an alkali treated zeolite, is less prone to producing organic chlorides and performs much better in such chloride removal service, also adsorbing organic chloride compounds, while capable of reaching chloride loadings of up to for example about 20-22% wt on the adsorbent, expressed on a dry and chloride-free basis. We prefer to use a chloride adsorbent based on an alkali-treated zeolite, more particularly a zeolite having a pH of at least 10, preferably 11, when measured in slurry. The adsorbent may comprise other components such as magnesium aluminosilicate, and binder material, and may be in the form of spheres or extrudates. An example of a suitable alkaline zeolite is product NB 316 from CLS Industrial Purification, containing from 70-90% wt of zeolite and sodium oxide and from 10-30% magnesium aluminosilicate and having a body centre cubic crystal structure, a pH of 11, a nominal pore size of 10 Angstroms, and a surface area of 630 m2/g. The product is available as 1.6 mm diameter (1/16") spheres or as 1.6 mm (1/16"), 3.2 mm (1/8") or 4.8 mm (3/16") diameter cylinders. The zeolite of the adsorbent may be of mineral origin, or may be synthetic. The zeolite may have one single crystal structure, or be a mixture of zeolites with different crystal structures. We prefer to use a mixture of faujasite, having larger 12-ring pores, and Linde Zeolite A, which as smaller 8-ring pores. The adsorbent preferably comprises a binder material in addition to the zeolite, but could be binderless. Clay is a suitable binder material, such as chlorite. The adsorbent may be formulated from fresh zeolite, or may be based on a waste byproduct from a different process using a suitable zeolite as catalyst or adsorbent material, preferably after regeneration such as by oxidative regeneration. We prefer to use an adsorbent having a large surface area, such as at least 300 $m^2/g$, preferably at least 400 $m^2/g$, more preferably at least 450 $m^2/g$, typically 488 $m^2/g$. Higher surface areas are also suitable, such as 500 $m^2/g$ or 600 $m^2/g$ and above. The activity and capacity of the adsorbent is preferably increased by treatment with an alkali solution, typically containing NaOH, $Ca(OH)_2$, KOH or a mixture thereof.

We prefer that only the hydrogen supply to the more sensitive consumers is treated with the alkali treated molecular sieve, so that the amount of generated spent adsorbent can be minimised. The catalytic reforming hydrogen going to the less sensitive consumers may preferably undergo only the conventional cleanup. When an activated alumina adsorbent is used for this conventional cleanup, we prefer to withdraw the hydrogen for treatment with the alkali treated molecular sieve upstream of the activated alumina adsorbent, so that the amount of organic chlorides in the hydrogen to be treated with the alkali treated molecular sieve is minimised. What is described here for hydrogen from a catalytic reforming processes is equally applicable to hydrogen from other sources that may contain chlorides for instance because of chloride being present in at least one their feedstocks.

The invention is now further illustrated with the following example.

EXAMPLE 1

This example illustrates the differences between various absorption liquids in terms of their vapour-liquid distribution coefficient for hydrocobalt tetracarbonyl, continuous hydroformylation reaction unit having three stirred tank reactors in series was operated in steady state on mixed nonene feed with, located downstream of a high pressure product cooler and a gas separator, a stripper for stripping $HCo(CO)_4$ from the oxo product. The mixed nonene feed had been obtained by the oligomerisation of propylene using a solid phosphoric acid catalyst. By feeding a constant flow of olefin feed to the hydroformylation section, having a constant cobalt concentration, and by applying constant operating parameters on the stripper in terms of temperature, stripping gas rate and pressure, a vapour stream with a steady concentration of cobalt as $HCo(CO)_4$ could be established from the stripper overhead. The cobalt containing vapour from the stripper was sent to, in series:

1. a cold liquid trap to prevent organic liquid getting through into the downstream scrubbers,
2. a front-end bubbler or gas scrubber, provided with temperature and pressure control, and which was filled with the desired scrubbing liquid for being tested,
3. a back-end bubbler operating at atmospheric pressure and filled with a caustic solution, to collect all the $HCo(CO)_4$ that may come through from the front end bubbler, and
4. a wet gas meter to measure the gas flow.

The sum of the cobalt that accumulates in both bubblers during a particular test period was determined, and using the cumulative gas flow during that same period converted into the amount and concentration of cobalt in the vapor stream from the stripper.

Each experiment ran for a time of about 24 hours to assure that an equilibrium over the scrubber was established, confirmed by measuring the same cobalt concentration in the two vapour streams (inlet and outlet of the front-end bubbler). It was assumed that under these conditions the absorption liquid in the scrubber vessel was saturated with $HCo(CO)_4$. The liquid in the scrubber was then sampled and analysed for its cobalt content. The cobalt concentrations in vapour and liquid were all converted to mole fraction.

The ratio of the cobalt concentrations in the vapour divided by that in the liquid was derived to give the "apparent" vapour-liquid distribution coefficient for hydrocobalt tetracarbonyl for the particular absorption liquid and at the temperature of measurement. The selection of absorption liquids, the scrubber temperatures, the cobalt concentrations expressed in mole % and the dimensionless gas/liquid distribution coefficient for $HCo(CO)_4$ at the indicated scrubber temperature are shown in Table 1. All experiments were performed with a pressure of 5 bar absolute in the scrubber. It is expected that at higher pressures a lower vapour-liquid distribution coefficient would be measured for the same liquid and temperature.

TABLE 1

| Absorption Liquid | Temp °C. | Mol % Cobalt in Gas | Mol % Cobalt in Liquid | Gas/liquid Distrib. Coeff. |
|---|---|---|---|---|
| Water with 1% wt free formic acid | 36 | 0.112 | 0.033 | 3.35 |
| Water with 1% wt free formic acid | 50 | 0.100 | 0.030 | 3.36 |
| Water with 0.4% wt $Co^{2+}$ as cobalt formate and 2.5% wt free formic acid | 50 | 0.068 | 0.115 | 0.59 |
| Water with 0.4% wt $Co^{2+}$ as cobalt formate and 3.0% wt free formic acid | 80 | 0.060 | 0.074 | 0.81 |
| Water with 0.2% wt $Co^{2+}$ as cobalt formate and 2.5% wt free formic acid | 50 | 0.080 | 0.062 | 1.3 |
| Water with 0.2% wt $Co^{2+}$ as cobalt formate and 3.0% wt free formic acid | 50 | 0.033 | 0.032 | 1.01 |
| Cobalt-depleted organic oxo product | 50 | 0.032 | 0.351 | 0.09 |

The first two experiments with only dilute formic acid reflect the poorer absorption efficiency of $HCo(CO)_4$ in a simple acidic aqueous phase. Any temperature effect on such a scrubbing liquid appears to be small, if present.

The results show the significant beneficial impact of having a cation present, in this case $Co^{2+}$, when the absorption liquid is aqueous. This advantage improves with higher concentrations of the cation. It may also be seen that a lower, i.e. a more "favourable", distribution coefficient is obtained at a lower temperature. It may also be observed that an organic absorption liquid has yet a significantly more favourable distribution coefficient for cobalt carbonyl absorption than an aqueous cation-containing liquid. It is believed that the organic liquid is more effective because it is able to dissolve any $Co_2(CO)_8$ that may be formed and thus may provide a sink for cobalt carbonyls that is not available in an aqueous scrubbing liquid.

Having now fully described this invention, it will be appreciated by those skilled in the art that the invention can be performed within a wide range of parameters within what is claimed, without departing from the spirit and scope of the invention.

The invention claimed is:

1. A process for producing a $C_6$-$C_{15}$ oxygenate by hydroformylating a $C_5$-$C_{14}$ olefin feed in the presence of a hydroformylation catalyst comprising a first metal that is cobalt, to form an organic cobalt-containing hydroformylation reaction product (1), which process comprises a demetalling step for removing cobalt from the reaction product (1) thereby producing a cobalt-containing aqueous product (2) and an organic cobalt-depleted reaction product (3), and in which process a gas stream (4) containing volatile cobalt carbonyl is separated from the reaction product (1) and the gas stream (4) is treated with an absorption liquid for absorbing at least part of the volatile cobalt carbonyl contained in the gas, thereby forming a cobalt-containing absorption liquid, characterised in that the cobalt-containing absorption liquid is recycled to the demetalling step.

2. The process according to claim 1 wherein the absorption liquid has a vapour-liquid distribution coefficient for hydrocobalt tetracarbonyl at 50° C. of at most 3.0.

3. The process according to claim 1 wherein the absorption liquid is organic.

4. The process according to claim 3 wherein the absorption liquid comprises at least part of the organic cobalt-depleted reaction product (3) or at least part of a derivative thereof selected from one or more of the group consisting of (i) a light fraction separated from the reaction product (3), (ii) a heavy fraction separated from the reaction product (3), (iii) a hydrogenation product obtained by hydrogenating at least part of the reaction product (3), (iv) a light fraction separated from such hydrogenation product and (v) a heavy fraction separated from such hydrogenation product.

5. The process according to claim 1 wherein the absorption liquid is aqueous, and optionally contains a first acid.

6. The process according to claim 5 wherein the absorption liquid comprises an aqueous solution of a salt of a second metal with a second acid having a first pKa of at least 1.5 at 25° C.

7. The process according to claim 6 wherein the salt is cobalt formate.

8. The process according to claim 1 wherein the demetalling step comprises
   (a) contacting the reaction product (1) with an aqueous solution of a third acid to form an aqueous solution of the cobalt salt of the third acid as the cobalt-containing aqueous product (2), and the organic cobalt-depleted reaction product (3).

9. The process according to claim 8 wherein the contacting (a) is performed in the presence of an oxygen-containing gas or an oxygen-donating compound.

10. The process according to claim 1 wherein the demetalling step comprises
   (b) contacting the reaction product (1) with an aqueous solution of a salt of a third metal with a fourth acid having a first pKa of at least 1.5 at 25° C., to form an aqueous solution (5) comprising the metal salt of cobalt carbonyl, and
   wherein the contacting (b) is performed prior to contacting (a) when contacting (a) is present.

11. The process according to claim 10 wherein the third metal is cobalt, further comprising recycling at least part of the aqueous solution (5) to the hydroformylation reaction.

12. The process according to claim 1 further comprising hydrogenating the reaction product (3) and recovering an alcohol product from the hydrogenation product.

13. The process according to claim 12 further comprising esterifying the alcohol product with an acid or anhydride to form an ester.

14. The process according to claim 13 wherein the acid or anhydride is selected from benzoic acid, phthalic acid, adipic acid, trimellitic acid, cyclohexanoic acid, cyclohexanoic dibasic acid, pyromellitic acid and their respective anhydrides, and mixtures of any two or more thereof.

15. The process according to claim 14 wherein the ester is a phthalate and further comprising hydrogenating the phthalate ester to a hexahydrophthalate ester.

16. The process according to claim 5 wherein the first acid is formic acid.

17. The process according to claim 1 wherein the absorption liquid is not an olefin feed.

* * * * *